(12) United States Patent
Chanduszko et al.

(10) Patent No.: US 8,480,706 B2
(45) Date of Patent: Jul. 9, 2013

(54) TUBULAR PATENT FORAMEN OVALE (PFO) CLOSURE DEVICE WITH CATCH SYSTEM

(75) Inventors: Andrzej J. Chanduszko, Chandler, AZ (US); David J. Callaghan, Boston, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 1274 days.

(21) Appl. No.: 11/395,718

(22) Filed: Mar. 31, 2006

(65) Prior Publication Data
US 2007/0010851 A1   Jan. 11, 2007

Related U.S. Application Data

(63) Continuation-in-part of application No. 10/890,784, filed on Jul. 14, 2004, now Pat. No. 7,678,123.

(60) Provisional application No. 60/486,992, filed on Jul. 14, 2003.

(51) Int. Cl.
*A61B 17/08*   (2006.01)
*A61D 1/00*   (2006.01)

(52) U.S. Cl.
USPC .......................................... 606/213; 606/151

(58) Field of Classification Search
USPC ... 606/213, 139–142, 151, 157–158; 128/831
See application file for complete search history.

(56) References Cited

U.S. PATENT DOCUMENTS

| | | | |
|---|---|---|---|
| 3,824,631 | A | 7/1974 | Burstein et al. |
| 3,874,388 | A | 4/1975 | King et al. |
| 3,875,648 | A | 4/1975 | Bone |
| 3,924,631 | A | 12/1975 | Mancusi, Jr. |

(Continued)

FOREIGN PATENT DOCUMENTS

| | | |
|---|---|---|
| DE | 94 13 645 U1 | 10/1994 |
| DE | 9413645 U1 | 10/1994 |

(Continued)

OTHER PUBLICATIONS

Meier, MD, Bernhard et al., "Contemporary Management of Patent Foramen Ovale," American Heart Association, Inc., Circulation, 2003, vol. 107, pp. 5-9.

(Continued)

*Primary Examiner* — Corrine M McDermott
*Assistant Examiner* — Mark Mashack
(74) *Attorney, Agent, or Firm* — DLA Piper LLP (US)

(57) ABSTRACT

The present invention provides a device for occluding an anatomical aperture, such as an atrial septal defect (ASD) or a patent foramen ovale (PFO). The occluder includes two sides connected by a central tube. The occluder is formed from a tube, which is cut to produce struts in each side. Upon the application of force, the struts deform into loops. The loops may be of various shapes, sizes, and configurations, and, in at least some embodiments, the loops have rounded peripheries. In some embodiments, at least one of the sides includes a tissue scaffold. The occluder further includes a catch system that maintains its deployed state in vivo. When the occluder is deployed in vivo, the two sides are disposed on opposite sides of the septal tissue surrounding the aperture and the catch system is deployed so that the occluder exerts a compressive force on the septal tissue and closes the aperture.

12 Claims, 17 Drawing Sheets

U.S. PATENT DOCUMENTS

| | | | |
|---|---|---|---|
| 4,006,747 A | 2/1977 | Kronenthal et al. | |
| 4,007,743 A | 2/1977 | Blake | |
| 4,149,327 A | 4/1979 | Hammer et al. | |
| 4,425,908 A | 1/1984 | Simon | |
| 4,610,674 A | 9/1986 | Suzuki et al. | |
| 4,626,245 A | 12/1986 | Weinstein | |
| 4,693,249 A | 9/1987 | Schenck et al. | |
| 4,696,300 A | 9/1987 | Anderson | |
| 4,710,181 A | 12/1987 | Fuqua | |
| 4,710,192 A | 12/1987 | Liotta et al. | |
| 4,738,666 A | 4/1988 | Fuqua | |
| 4,836,204 A | 6/1989 | Landymore et al. | |
| 4,840,623 A | 6/1989 | Quackenbush | |
| 4,902,508 A | 2/1990 | Badylak et al. | |
| 4,915,107 A | 4/1990 | Rebuffat et al. | |
| 4,917,089 A | 4/1990 | Sideris | |
| 4,921,479 A | 5/1990 | Grayzel | |
| 4,956,178 A | 9/1990 | Badylak et al. | |
| 5,021,059 A | 6/1991 | Kensey et al. | |
| 5,037,433 A | 8/1991 | Wilk et al. | |
| 5,041,129 A | 8/1991 | Hayhurst et al. | |
| 5,049,131 A | 9/1991 | Deuss | |
| 5,078,736 A | 1/1992 | Behl | |
| 5,106,913 A | 4/1992 | Yamaguchi et al. | |
| 5,108,420 A * | 4/1992 | Marks | 606/213 |
| 5,149,327 A | 9/1992 | Oshiyama | |
| 5,163,131 A | 11/1992 | Row et al. | |
| 5,167,363 A | 12/1992 | Adkinson et al. | |
| 5,167,637 A | 12/1992 | Okada et al. | |
| 5,171,259 A | 12/1992 | Inoue | |
| 5,176,659 A | 1/1993 | Mancini | |
| 5,192,301 A | 3/1993 | Kamiya et al. | |
| 5,222,974 A | 6/1993 | Kensey et al. | |
| 5,226,879 A | 7/1993 | Ensminger et al. | |
| 5,236,440 A | 8/1993 | Hlavacek | |
| 5,245,023 A | 9/1993 | Peoples et al. | |
| 5,245,080 A | 9/1993 | Aubard et al. | |
| 5,250,430 A | 10/1993 | Peoples et al. | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | |
| 5,316,262 A | 5/1994 | Koebler | |
| 5,320,611 A | 6/1994 | Bonutti et al. | |
| 5,334,217 A | 8/1994 | Das | |
| 5,350,363 A | 9/1994 | Goode et al. | |
| 5,350,399 A * | 9/1994 | Erlebacher et al. | 606/213 |
| 5,354,308 A | 10/1994 | Simon et al. | |
| 5,364,356 A | 11/1994 | Hofling | |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,453,099 A | 9/1995 | Lee et al. | |
| 5,478,353 A | 12/1995 | Yoon | |
| 5,480,353 A | 1/1996 | Garza, Jr. | |
| 5,480,424 A | 1/1996 | Cox | |
| 5,486,193 A | 1/1996 | Bourne et al. | |
| 5,507,811 A | 4/1996 | Koike et al. | |
| 5,534,432 A | 7/1996 | Peoples et al. | |
| 5,540,712 A | 7/1996 | Kleshinski et al. | |
| 5,562,632 A | 10/1996 | Davila et al. | |
| 5,577,299 A | 11/1996 | Thompson et al. | |
| 5,601,571 A | 2/1997 | Moss | |
| 5,603,703 A | 2/1997 | Elsberry et al. | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,649,959 A | 7/1997 | Hannam et al. | |
| 5,663,063 A | 9/1997 | Peoples et al. | |
| 5,683,411 A | 11/1997 | Kavteladze et al. | |
| 5,690,674 A | 11/1997 | Diaz | |
| 5,693,085 A | 12/1997 | Buirge et al. | |
| 5,702,421 A * | 12/1997 | Schneidt | 606/213 |
| 5,709,707 A | 1/1998 | Lock et al. | |
| 5,713,864 A | 2/1998 | Verkaart | |
| 5,717,259 A | 2/1998 | Schexnayder | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,772,641 A | 6/1998 | Wilson | |
| 5,776,162 A | 7/1998 | Kleshinski | |
| 5,776,183 A | 7/1998 | Kanesaka et al. | |
| 5,797,960 A | 8/1998 | Stevens et al. | |
| 5,800,516 A | 9/1998 | Fine et al. | |
| 5,810,884 A | 9/1998 | Kim | |
| 5,820,594 A | 10/1998 | Fontirroche et al. | |
| 5,823,956 A | 10/1998 | Roth et al. | |
| 5,829,447 A | 11/1998 | Stevens et al. | |
| 5,853,420 A | 12/1998 | Chevillon et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,893,856 A | 4/1999 | Jacob et al. | |
| 5,902,287 A | 5/1999 | Martin | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,944,691 A | 8/1999 | Querns et al. | |
| 5,944,738 A | 8/1999 | Amplatz et al. | |
| 5,955,110 A | 9/1999 | Patel et al. | |
| 5,976,174 A | 11/1999 | Ruiz | |
| 5,980,505 A | 11/1999 | Wilson | |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,019,753 A | 2/2000 | Pagan | |
| 6,024,756 A | 2/2000 | Huebsch et al. | |
| 6,027,519 A | 2/2000 | Stanford | |
| 6,030,007 A | 2/2000 | Bassily et al. | |
| 6,056,760 A | 5/2000 | Koike et al. | |
| 6,071,998 A | 6/2000 | Muller et al. | |
| 6,077,291 A | 6/2000 | Das | |
| 6,077,880 A | 6/2000 | Castillo et al. | |
| 6,079,414 A | 6/2000 | Roth | |
| 6,080,182 A | 6/2000 | Shaw et al. | |
| 6,096,347 A | 8/2000 | Geddes et al. | |
| 6,106,913 A | 8/2000 | Scardino et al. | |
| 6,113,609 A | 9/2000 | Adams | |
| 6,117,159 A | 9/2000 | Huebsch et al. | |
| 6,126,686 A | 10/2000 | Badylak et al. | |
| 6,132,438 A | 10/2000 | Fleischman et al. | |
| 6,143,037 A | 11/2000 | Goldstein et al. | |
| 6,152,144 A | 11/2000 | Lesh et al. | |
| 6,165,183 A | 12/2000 | Kuehn et al. | |
| 6,165,204 A | 12/2000 | Levinson et al. | |
| 6,168,588 B1 | 1/2001 | Wilson | |
| 6,171,329 B1 | 1/2001 | Shaw et al. | |
| 6,174,322 B1 | 1/2001 | Schneidt et al. | |
| 6,174,330 B1 | 1/2001 | Stinson | |
| 6,183,443 B1 | 2/2001 | Kratoska et al. | |
| 6,187,039 B1 | 2/2001 | Hiles et al. | |
| 6,190,353 B1 | 2/2001 | Makower et al. | |
| 6,190,357 B1 | 2/2001 | Ferrari et al. | |
| 6,197,016 B1 | 3/2001 | Fourkas et al. | |
| 6,199,262 B1 | 3/2001 | Martin | |
| 6,206,895 B1 | 3/2001 | Levinson | |
| 6,206,907 B1 | 3/2001 | Marino et al. | |
| 6,214,029 B1 | 4/2001 | Thill et al. | |
| 6,217,590 B1 | 4/2001 | Levinson | |
| 6,221,092 B1 | 4/2001 | Koike et al. | |
| 6,227,139 B1 | 5/2001 | Nguyen et al. | |

| | | |
|---|---|---|
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1* | 11/2001 | Huebsch et al. ............... 606/213 |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,358,238 B1 | 3/2002 | Sherry |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,363 B1* | 4/2002 | Herrington et al. ............... 606/79 |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,450,987 B1 | 9/2002 | Kramer |
| 6,460,749 B1 | 10/2002 | Levinson et al. |
| 6,482,224 B1 | 11/2002 | Michler et al. |
| 6,488,706 B1 | 12/2002 | Solymar et al. |
| 6,494,846 B1 | 12/2002 | Margolis |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,719 B2 | 7/2003 | Wang |
| 6,585,755 B2 | 7/2003 | Jackson et al. |
| 6,596,013 B2* | 7/2003 | Yang et al. ............... 606/215 |
| 6,599,448 B1 | 7/2003 | Ehrhard, Jr. et al. |
| 6,610,764 B1 | 8/2003 | Martin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,828,357 B1 | 12/2004 | Martin et al. |
| 6,838,493 B2 | 1/2005 | Williams et al. |
| 6,860,895 B1* | 3/2005 | Akerfeldt et al. ............... 606/215 |
| 6,867,247 B2 | 3/2005 | Williams et al. |
| 6,867,248 B1 | 3/2005 | Martin et al. |
| 6,867,249 B2 | 3/2005 | Lee |
| 6,921,410 B2 | 7/2005 | Porter |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1* | 12/2002 | Wahr et al. ............... 606/213 |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0120337 A1 | 6/2003 | Van Tassel et al. |
| 2003/0139819 A1 | 7/2003 | Beer et al. |
| 2003/0171774 A1 | 9/2003 | Seigner et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0044364 A1* | 3/2004 | DeVries et al. ............... 606/213 |
| 2004/0073242 A1 | 4/2004 | Chanduszko |
| 2004/0133236 A1 | 7/2004 | Chanduszko |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1 | 2/2005 | Chanduszko |
| 2005/0113868 A1 | 5/2005 | Devellian |
| 2005/0267523 A1 | 12/2005 | Devellian et al. |
| 2005/0273135 A1 | 12/2005 | Chanduszko et al. |
| 2005/0288786 A1 | 12/2005 | Chanduszko |
| 2006/0122647 A1 | 6/2006 | Callaghan et al. |
| 2006/0265004 A1 | 11/2006 | Callaghan et al. |
| 2006/0271089 A1 | 11/2006 | Alejandro et al. |
| 2007/0010851 A1 | 1/2007 | Chanduszko et al. |
| 2007/0167981 A1 | 7/2007 | Opolski |

FOREIGN PATENT DOCUMENTS

| | | |
|---|---|---|
| EP | 0 362 113 A1 | 4/1990 |
| EP | 0362113 A1 | 4/1990 |
| EP | 0 474 887 A1 | 3/1992 |
| EP | 0474887 A1 | 3/1992 |
| EP | 0 839 549 A1 | 5/1998 |
| EP | 0839549 A1 | 5/1998 |
| EP | 0 861 632 | 9/1998 |
| EP | 1 013 227 A2 | 6/2000 |
| EP | 1013227 A2 | 6/2000 |
| EP | 1 046 375 A1 | 10/2000 |
| EP | 1046375 A1 | 10/2000 |
| EP | 1 222 897 A2 | 7/2002 |
| EP | 1222897 A2 | 7/2002 |
| WO | WO-96/25179 A1 | 8/1996 |
| WO | WO 96/25179 A1 | 8/1996 |
| WO | WO-96/31157 A1 | 10/1996 |
| WO | WO-98/07375 A1 | 2/1998 |
| WO | WO-98/08462 A2 | 3/1998 |
| WO | WO-98/16174 A1 | 4/1998 |
| WO | WO-98/29026 A2 | 7/1998 |
| WO | WO-98/51812 A2 | 11/1998 |
| WO | WO-99/05977 A1 | 2/1999 |
| WO | WO-98/18864 | 4/1999 |
| WO | WO-99/18862 A1 | 4/1999 |
| WO | WO-99/18864 A1 | 4/1999 |
| WO | WO-99/18870 A1 | 4/1999 |
| WO | WO-99/18871 A1 | 4/1999 |
| WO | WO-99/30640 A1 | 6/1999 |
| WO | WO-99/66846 | 12/1999 |
| WO | WO-00/27292 A1 | 5/2000 |
| WO | WO-00/44428 A2 | 8/2000 |
| WO | WO-01/08600 | 2/2001 |
| WO | WO-01/19256 | 3/2001 |
| WO | WO-01/21247 A1 | 3/2001 |
| WO | WO-01/28432 | 4/2001 |
| WO | WO-01/30268 A1 | 5/2001 |
| WO | WO 01/49185 * | 7/2001 |
| WO | WO-01/49185 A1 | 7/2001 |
| WO | WO-01/78596 A1 | 10/2001 |
| WO | WO-01/93783 | 12/2001 |
| WO | WO-02/17809 A1 | 3/2002 |
| WO | WO-02/24106 A3 | 3/2002 |
| WO | WO-03/024337 A1 | 3/2003 |
| WO | WO-03/053493 A2 | 7/2003 |
| WO | WO-03/059152 A2 | 7/2003 |
| WO | WO-03/063732 A2 | 8/2003 |
| WO | WO-03/077733 A2 | 9/2003 |
| WO | WO-03/082076 A2 | 10/2003 |
| WO | WO-03/103476 A2 | 12/2003 |
| WO | WO-2004/032993 A2 | 4/2004 |
| WO | WO-2004/037333 A1 | 5/2004 |
| WO | WO-2004/043266 A2 | 5/2004 |
| WO | WO-2004/043508 A1 | 5/2004 |
| WO | WO-2004/052213 A1 | 6/2004 |
| WO | WO-2005/006990 A2 | 1/2005 |
| WO | WO-2005/018728 A2 | 3/2005 |
| WO | WO-2005/027752 A1 | 3/2005 |
| WO | WO-2005/074813 A1 | 8/2005 |
| WO | WO-2005/092203 A1 | 10/2005 |
| WO | WO-2005/110240 A1 | 11/2005 |
| WO | WO-2005/112779 A1 | 12/2005 |
| WO | WO-2006/036837 | 4/2006 |
| WO | WO-2006/036837 A2 | 4/2006 |
| WO | WO-2006/102213 A1 | 9/2006 |

OTHER PUBLICATIONS

European Examination Report, European Application No. 03729663.9, mailed Jul. 16, 2008 (5 Pages).

European Examination Report, European Application No. 03731562.9, mailed Jul. 18, 2008 (3 Pages).

European Examination Report, European Application No. 03779297.5, mailed Mar. 15, 2007 (6 Pages).

European Examination Report, European Application No. 04781644.2, mailed Aug. 23, 2007 (3 Pages).

European Search Report, European Application No. 03729663.9, mailed Feb. 20, 2008 (3 Pages).

International Search Report and Written Opinion, International Patent Application No. PCT/US06/41255, mailed Jun. 13, 2008 (6 pgs).

International Search Report and Written Opinion, International Patent Application No. PCT/US08/59429, mailed Sep. 5, 2008 (9 pgs).

International Search Report for International Patent Application No. PCT/AU03/00759, filed Jun. 19, 2003.

International Search Report, International Application No. PCT/US05/34276, mailed Oct. 9, 2007.

International Search Report, International Application No. PCT/US07/065546, mailed Oct. 29, 2007. 4 pages.

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17390, mailed Oct. 6, 2003 (4 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US03/35479, mailed Apr. 14, 2004 (2 pgs).

International Search Report, International Application No. PCT/US03/35998 mailed Jun. 16, 2004 (5 pgs).

International Search Report, International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US06/009978, mailed Jul. 13, 2006 (2 pgs).

International Search Report, International Application No. PCT/US2007/065526, mailed Aug. 8, 2007 (5 pgs).

International Search Report, International Application No. PCT/US2007/065541, mailed Aug. 7, 2007 (3 pgs).

International Search Report, International Application No. PCT/US97/14822, mailed Feb. 20, 1998 (2 pgs).

International Search Report, International Application No. PCT/US97/17927, mailed Feb. 10, 1998 (1 pg).

Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.

Kimura, A., et al., "Effects of Neutron Irradiation on the Transformation Behavior in Ti-Ni Alloys," Abstract, Proceedings of the Int'l Conf. on Mariensitic Transformations, 1992, pp. 935-940.

Klima, U., "Magnetic Vascular Port in Minimally Invasive Direct Coronary Artery Bypass Grafting," Circulation, 2004, II-55-II-60.

Nat'l Aeronautics and Space Administration, "55-Nitinol—The Alloy with a Memory: Its Physical Metallurgy, Properties and Applications," NASA Report, pp. 24-25.

Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.

Ramanathan, G., et al., "Experimental and Computational Methods for Shape Memory Alloys," 15th ASCE Engineering Mechanics Conference, Jun. 2-5, 2002.

Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.

Ruiz, et al., "The Puncture Technique: A New Method for Transcatheter Closure of Patent Foramen Ovale," Catheterization and Cardiovascular Interventions, 2001, vol. 53, pp. 369-372.

Shabalovskaya, S., "Surface, Corrosion amd Biocompatibility Aspects of Nitinol as and Implant Material," Bio-Medical Materials and Engineering, 2002, vol. 12, pp. 69-109.

SMST-2000, "Proceedings of the International Conference on Shape Memory and Superelastic Technologies," Apr. 30 to May 4, 2000, Asilomar Conference Center.

Stockel, "Nitinol Medical Devices and Implants," SMST-2000 Conference Proceedings, 2001, pp. 531-541.

Uchil, J., "Shape Memory Alloys—Characterization Techniques," Pramana—Journal of Physics, 2002, vol. 58(5)(6), pp. 1131-1139.

Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

\* cited by examiner

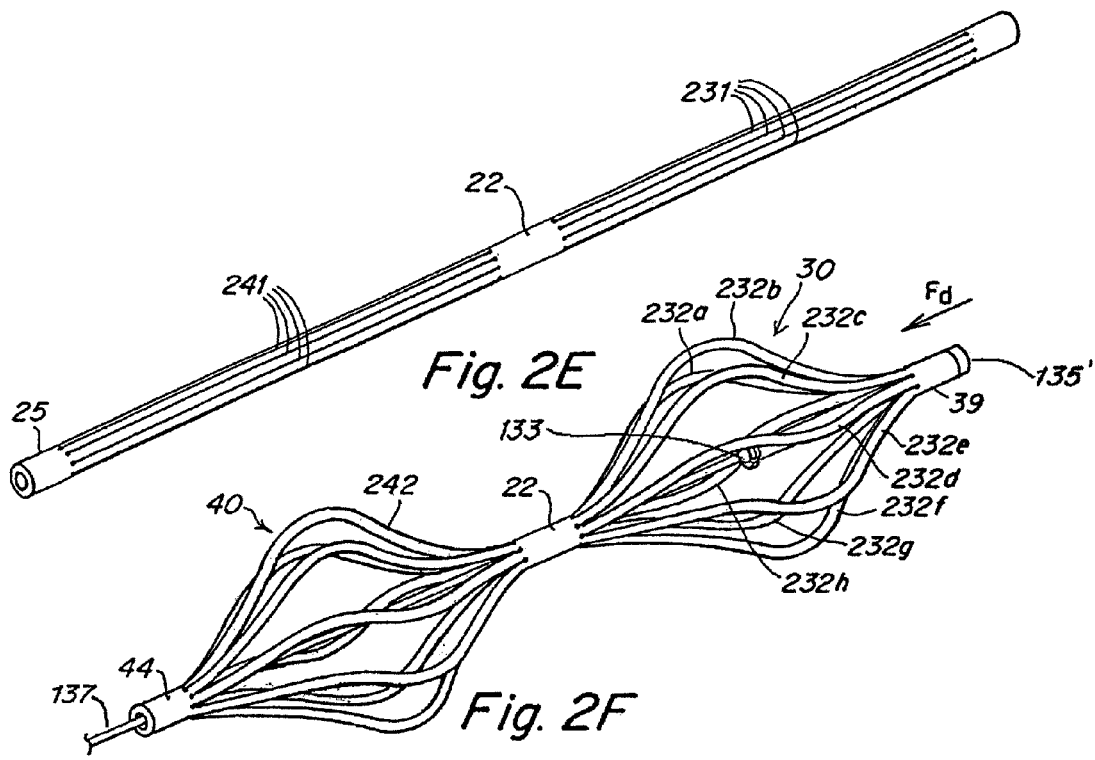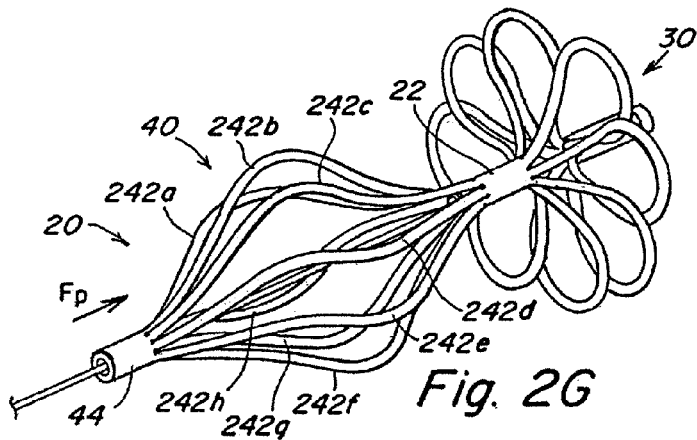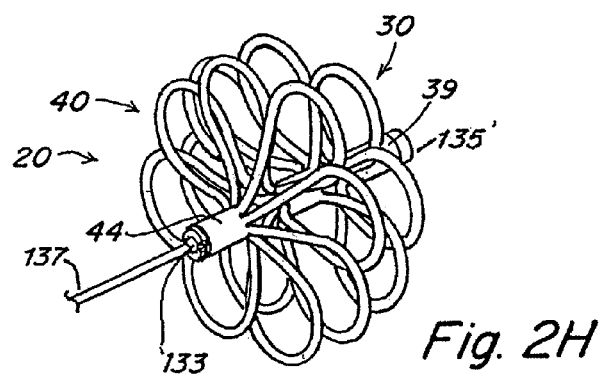

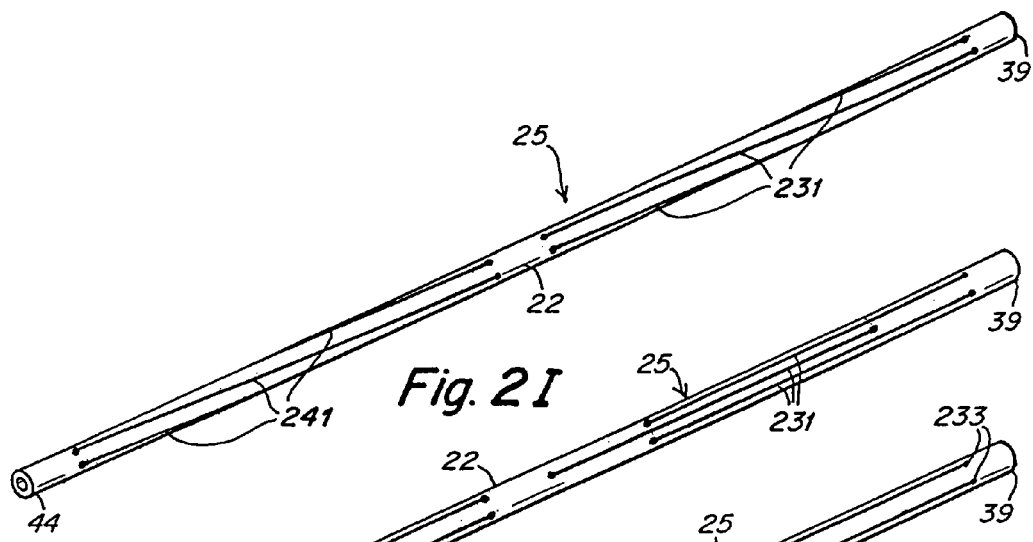
Fig. 2I
Fig. 2J
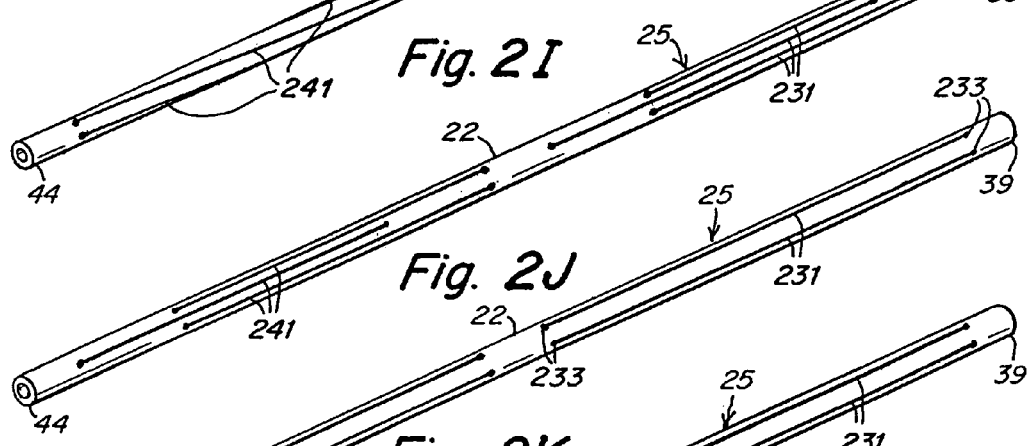
Fig. 2K
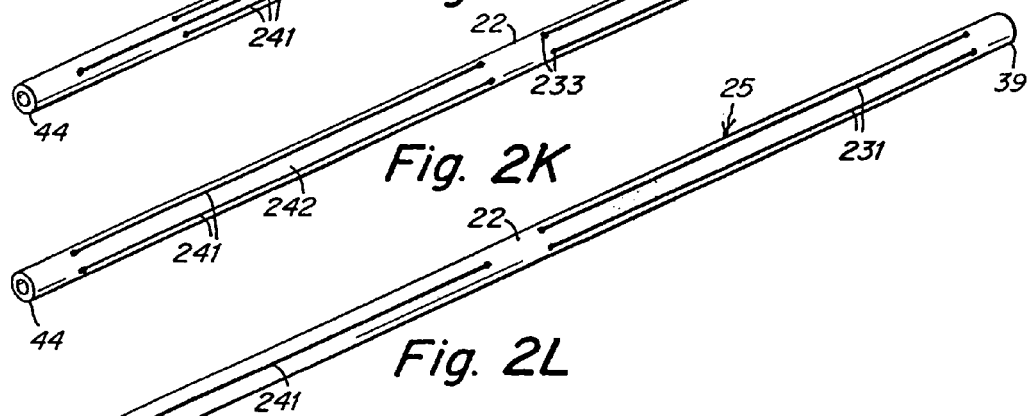
Fig. 2L
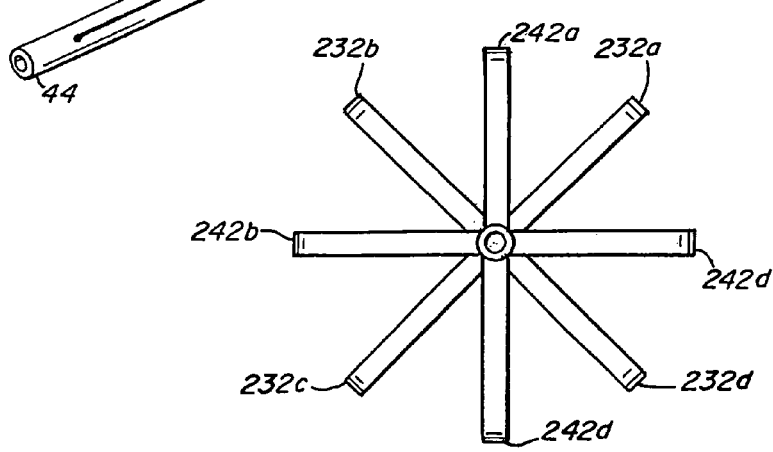
Fig. 2M

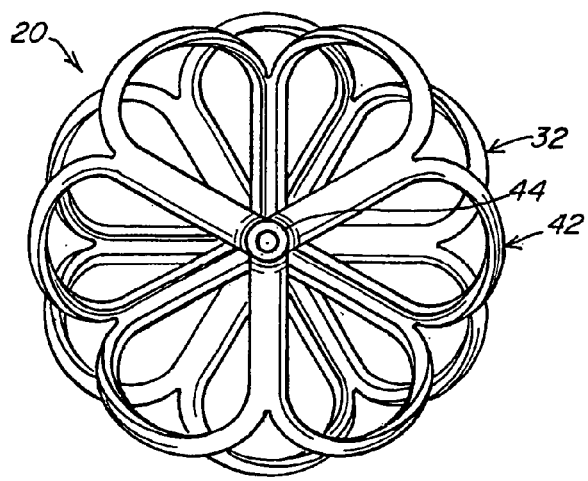
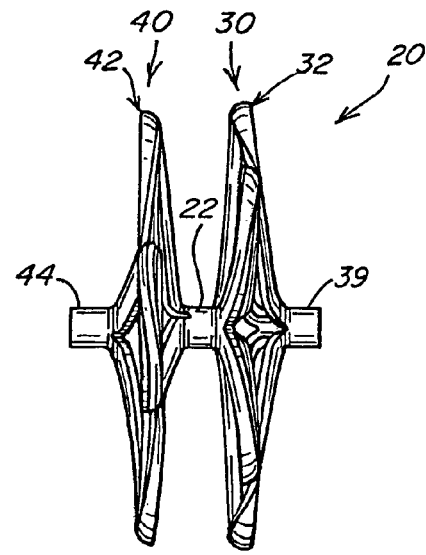
Fig. 4A　　　Fig. 4B
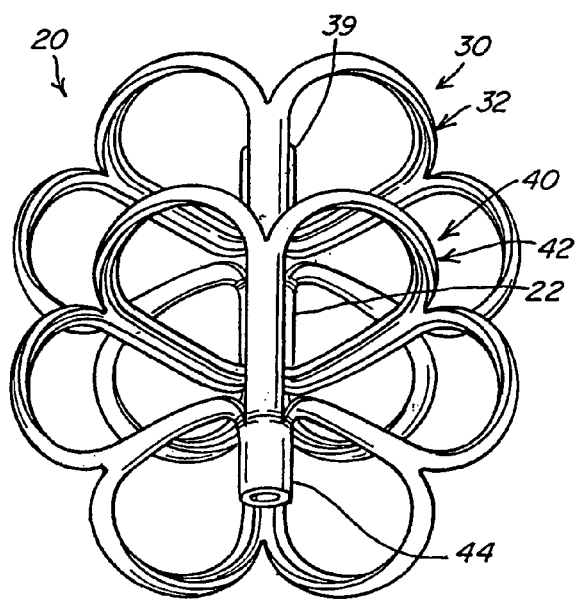
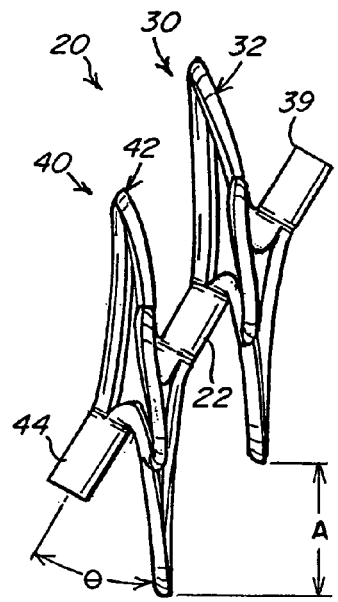
Fig. 5A　　　Fig. 5B

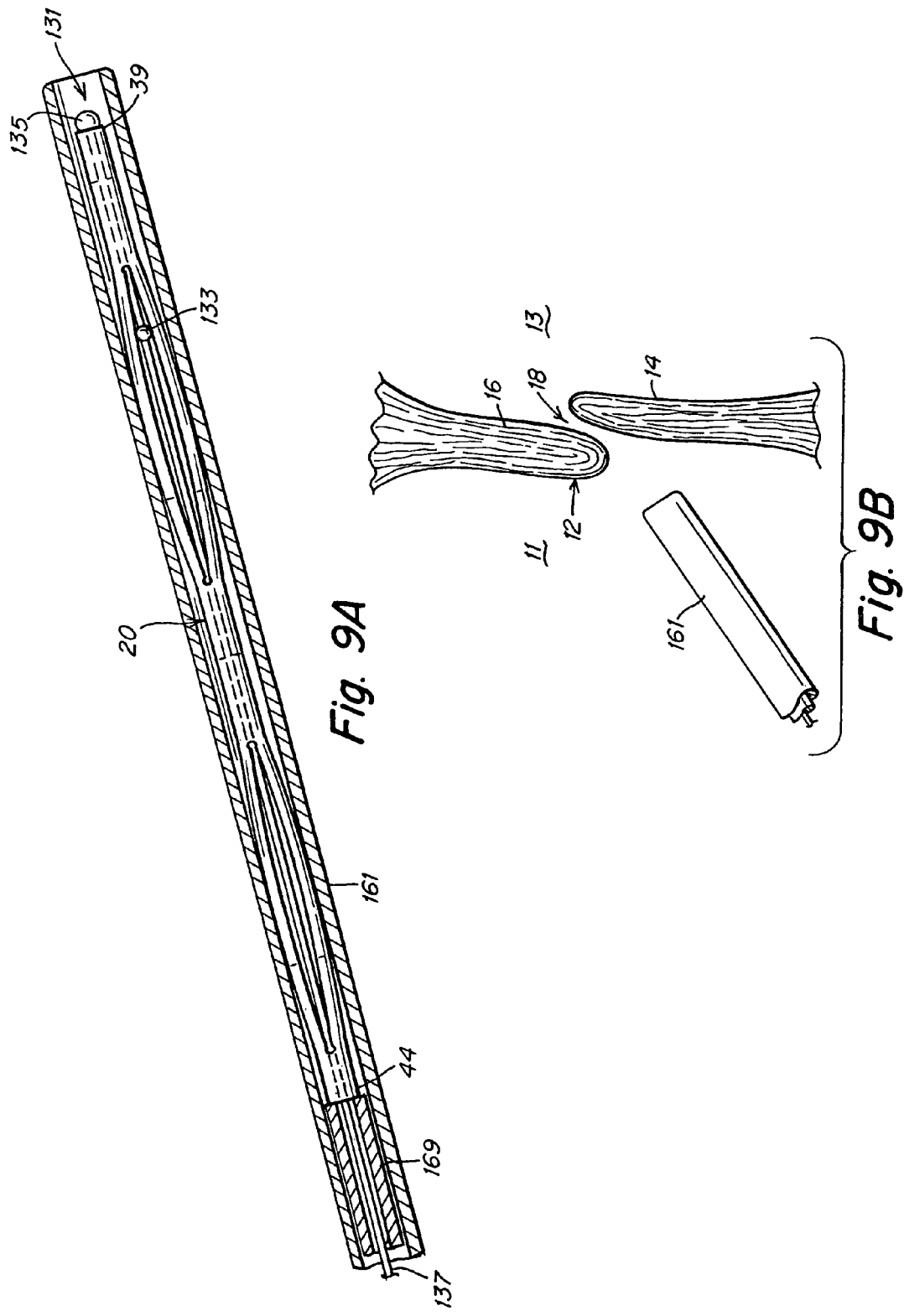

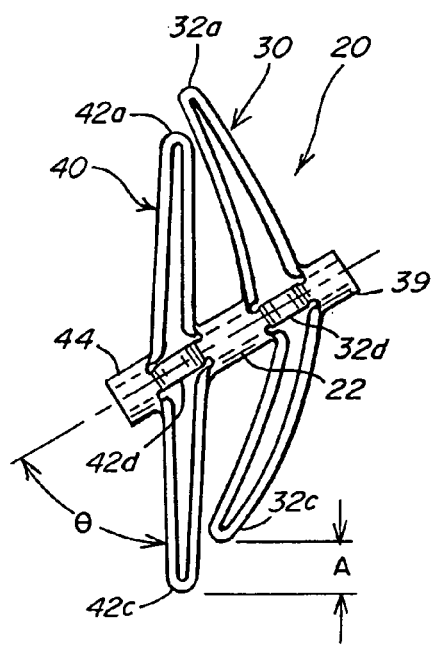
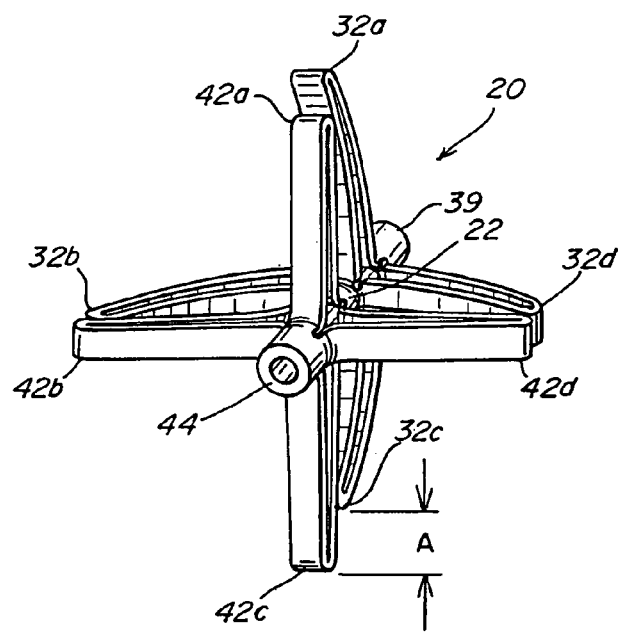
Fig. 11    Fig. 12
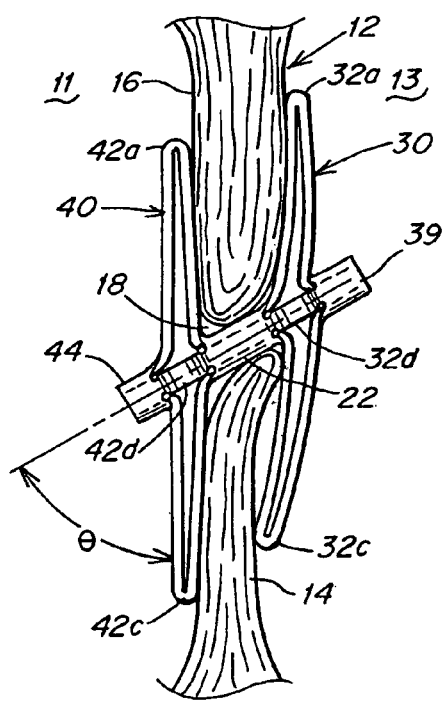
Fig. 13

TUBULAR PATENT FORAMEN OVALE (PFO) CLOSURE DEVICE WITH CATCH SYSTEM

REFERENCE TO RELATED APPLICATIONS

This application is a continuation-in-part of U.S. patent application Ser. No. 10/890,784, filed Jul. 14, 2004 and issued as U.S. Pat. No. 7,678,123, which claims the benefit of priority to U.S. Provisional Patent Application Ser. No. 60/486,992, filed Jul. 14, 2003, the disclosures of which are incorporated by reference herein in their entirety.

FIELD OF THE INVENTION

The present invention relates generally to an occlusion device for the closure of physical anomalies, such as an atrial septal defect, a patent foramen ovale, and other septal and vascular defects.

BACKGROUND OF THE INVENTION

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating in utero. Because blood is oxygenated through the umbilical chord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are not insignificant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

The present invention is designed to address these and other deficiencies of prior art septal closure devices.

SUMMARY OF THE INVENTION

In one aspect, the present invention provides a device for occluding an aperture in septal tissue, including a first side adapted to be disposed on one side of the septal tissue and a second side adapted to be disposed on the opposite side of the septal tissue. The first and second sides are adapted to occlude the aperture upon deployment of the device at its intended delivery location. The device also includes a catch system that maintains the configuration of the device once it has been deployed.

According to some embodiments, the catch system reduces and maintains the axial length of the device. Also, varied constructions could be used to maintain the axial dimension of the device. In one form, catch elements such as, e.g., balls, attached to a delivery wire could be used to maintain the axial dimension of the device. In a different construction, a locking mechanism could be used. Preferably, if a locking mechanism is used, it secures both sides of the device in the locked position with a single locking element.

According to at least some embodiments, the device is formed from a tube. According to some embodiments, the tube includes a material selected from the group consisting of metals, shape memory materials, alloys, polymers, bioabsorbable polymers, and combinations thereof. In particular embodiments, the tube includes a shape memory polymer. According to some embodiments, the device is formed by cutting the tube.

According to some embodiments, at least one of the first and second sides of the device includes a tissue scaffold. According to some embodiments, the tissue scaffold includes a material selected from the group consisting of polyester fabrics, Teflon-based materials, polyurethanes, metals, polyvinyl alcohol (PVA), extracellular matrix (ECM) or other bioengineered materials, synthetic bioabsorbable polymeric scaffolds, collagen, and combinations thereof. In particular embodiments, the tissue scaffold includes nitinol.

According to some embodiments, the first and second sides of the device are connected by a central tube. According to some embodiments, the central tube is positioned so as to minimize distortion to the septal tissue surrounding the aperture. In particular embodiments, the central tube is positioned at an angle θ from the second side, and the angle θ is greater than 0 degrees and less than about 90 degrees.

In another aspect, the present invention provides a device for occluding an aperture in septal tissue, including a first side adapted to be disposed on one side of the septal tissue and a second side adapted to be disposed on the opposite side of the septal tissue. The first and second sides are adapted to occlude the defect when the device is deployed at its intended delivery location. Each of the first and second sides includes loops. The device further includes a catch system that maintains the configuration of the device once it has been deployed. The loops of the first and second sides and the catch system cooperate to provide a compressive force to the septal tissue surrounding the aperture.

According to some embodiments, each of the first and second sides includes at least two loops. In particular embodiments, each of the first and second sides includes four or six loops. Of course, the most desirable number of loops on each side will depend on a variety of anatomical and manufacturing factors.

According to some embodiments, the device also includes a central tube that connects the first and second sides. According to some embodiments, the central tube is positioned so as to minimize distortion to the septal tissue surrounding the aperture. In particular embodiments, the central tube is positioned at an angle θ from the second side, and the angle θ is greater than 0 degrees and less than about 90 degrees.

According to some embodiments, the device is formed from a tube. According to some embodiments, the tube includes a material selected from the group consisting of metals, shape memory materials, alloys, polymers, bioabsorbable polymers, and combinations thereof. In particular embodiments, the tube includes nitinol. In particular embodiments, the tube includes a shape memory polymer.

According to some embodiments, at least one of the first and second sides further includes a tissue scaffold. According to some embodiments, the tissue scaffold includes a material selected from the group consisting of polyester fabrics, Teflon-based materials, polyurethanes, metals, polyvinyl alcohol (PVA), extracellular matrix (ECM) or other bioengineered materials, synthetic bioabsorbable polymeric scaffolds, collagen, and combinations thereof. In particular embodiments, the tissue scaffold includes nitinol.

According to some embodiments, each of the loops includes a rounded edge at its periphery to minimize trauma to the septal tissue. In particular embodiments, the outer periphery of the device is circular.

In still another aspect, the present invention provides a method of making a device for occluding an aperture in septal tissue, including providing a tube having first and second ends and upper and lower portions, cutting at least four axially-extending openings in the upper portion of the tube, cutting at least four axially-extending openings in the lower portion of the tube. The openings in the upper and lower portions are separated by a central portion of the tube.

According to some embodiments, the tube includes a material selected from the group consisting of metals, shape memory materials, alloys, polymers, bioabsorbable polymers, and combinations thereof. In particular embodiments, the tube includes a shape memory polymer.

In yet another aspect, the present invention provides a method of occluding an aperture in septal tissue, including providing a tube having first and second ends and upper and lower portions in a delivery sheath. The tube includes at least four axially-extending openings in its upper portion and at least three axially-extending openings in its lower portion. The openings in the upper and lower portions are separated by a central portion of the tube. The deliver sheath is inserted into a right atrium of a heart, through the aperture in the septal tissue, and into the left atrium of the heart. The first end and the upper portion of the tube are deployed into the left atrium. The sheath is then retracted through the aperture and into the right atrium of the heart, where the second end and the lower portion of the tube are deployed into the right atrium. The sheath is then withdrawn from the heart. Of course, a catch system could be used to secure the device in a delivered (expanded) state. The catch system may have any or all the characteristics described in the specification. Further, other types of catch systems could be used to hold the device in the delivered state.

According to some embodiments, a force is applied to each of the first and second ends in an axial direction such that the axial length of the tube is reduced. The force applied to the first end is in a direction opposite to that of the force applied to the second end.

BRIEF DESCRIPTION OF THE DRAWINGS

FIGS. 2E-2H are isometric views of an embodiment of an occluder according to the present invention;

FIGS. 2I-2K are isometric views of occluders according to various embodiments of the invention;

FIGS. 2L and 2M are side and top views, respectively, of an alternate embodiment of an occluder according to the present invention;

FIGS. 4A-4B are front elevational and side views, respectively, of another embodiment of an occluder according to the present invention;

FIGS. 5A-5B are front and side views, respectively, of still another embodiment of an occluder according to the present invention;

FIGS. 9A-9H are side views of one method for delivering an occluder according to the present invention to a septal defect.

FIG. 11 is a side view of an embodiment of the occluder of the present invention;

FIG. 12 is an isometric view of an embodiment of the occluder of the present invention; and FIG. 13 is a side view of the occluder of FIGS. 2I-2K deployed in vivo.

DETAILED DESCRIPTION OF THE INVENTION

The present invention provides a device for occluding an aperture within body tissue. This device relates particularly to, but is not limited to, a septal occluder made from a polymer tube. In particular and as described in detail below, the occluder of the present invention may be used for closing an ASD or PFO in the atrial septum of a heart. Although the embodiments of the invention are described with reference to an ASD or PFO, one skilled in the art will recognize that the device and methods of the present invention may be used to treat other anatomical conditions. As such, the invention should not be considered limited in applicability to any particular anatomical condition.

Figure 1:
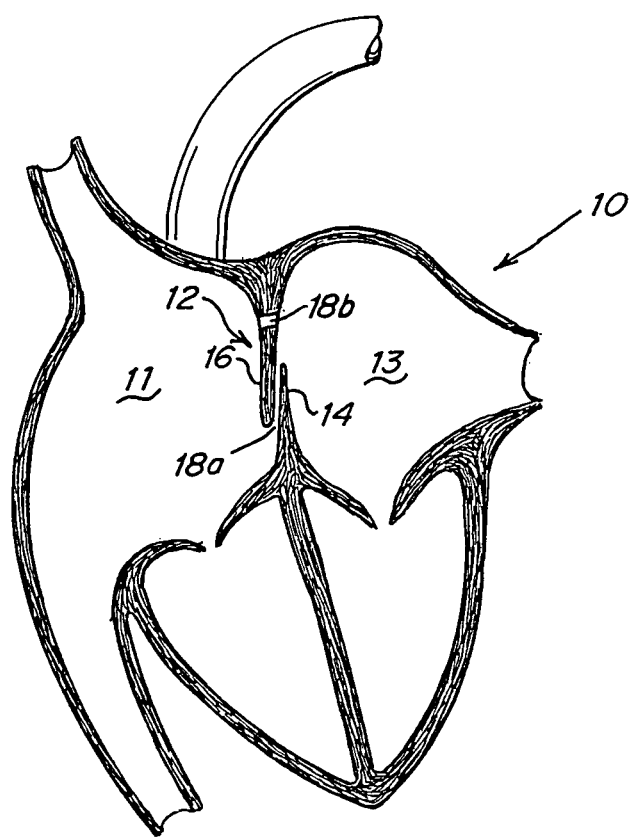
FIG. 1 is a schematic representation of a human heart including various septal defects.

FIG. 1 illustrates a human heart 10, having a right atrium 11 and a left atrium 13 and including various anatomical anomalies 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When a PFO is present, blood could travel through the passage 18a between septum primum 14 and septum secundum 16 (referred to as "the PFO tunnel"). Additionally or alternatively, the presence of an ASD could permit blood to travel through an aperture in the septal tissue, such as that schematically illustrated by aperture 18b.

The term "bioabsorbable," as used in this application, is also understood to mean "bioresorbable."

In this application, "distal" refers to the direction away from a catheter insertion location and "proximal" refers to the direction nearer the insertion location.

Referring to occluder 20, distal side 30 and proximal side 40 are connected by central tube 22. As illustrated, e.g., in FIGS. 9 and 10 the central tube 22 is an uncut central part of the tube used to form occluder 20. As described below, the entire tube is indicated by reference numeral 25. As shown in FIGS. 9 and 10, the occluder 20 may be inserted into the septal tissue 12 to prevent the flow of blood through the aperture 18a, e.g., the occluder may extend through the PFO tunnel such that the distal side 30 is located in the left atrium 13 and the proximal side 40 is located in the right atrium 11. Additionally or alternatively, the occluder 20 may be inserted into the septal tissue 12 so as to prevent the flow of blood through the aperture 18b, e.g., the occluder may extend through the ASD such that the distal side 30 is located in the left atrium 13 and the proximal side 40 is located in the right atrium 11. As used in this application, unless otherwise indicated, the term "aperture 18" refers to any anatomical anomaly that may be treated by use of occluder 20, such as PFO 18a or ASD 18b.

The occluder 20 is constructed of one or more metal or polymer tube(s), referred to collectively as "tube" 25. Tube 25 includes slits 31 and 41 (or 231 and 241), which are formed using an etching or cutting process that produces a particular cutting pattern on tube 25. For example, as shown in FIG. 2K, slits 31 (or 231) are cut along the axial length of the upper half of tube 25 using a cutting tool, e.g., a razor blade. According to some embodiments of the present invention and as shown in FIG. 2K, slits 31 (or 231) are cut without removing any significant amount of material from tube 25, i.e., the formation of slits 31 (or 231) does not significantly reduce the overall volume of tube 25. According to other embodiments of the present invention, slits 31 (or 231) are formed by cutting material out of tube 25 such that the volume of tube 25 is reduced. Both ends of each of slits 31 are rounded so as to relieve stresses at the axial ends of the slits 31. This prevents slits 31 from lengthening due to cyclic stresses present in a beating heart and the resultant material fatigue. In those embodiments where slits 31 are cut without removing any significant amount of material from tube 25, rounded ends or holes 33 may be produced by burning holes at both ends of each of slits 31. In those embodiments where slits 31 are formed by cutting material out of the tube 25, rounded ends 33 may be formed during the cutting process. The size of rounded ends 33 may vary depending upon the dimensions of tube 25 and the amount of stress release required by the deformation.

Figure 2A:
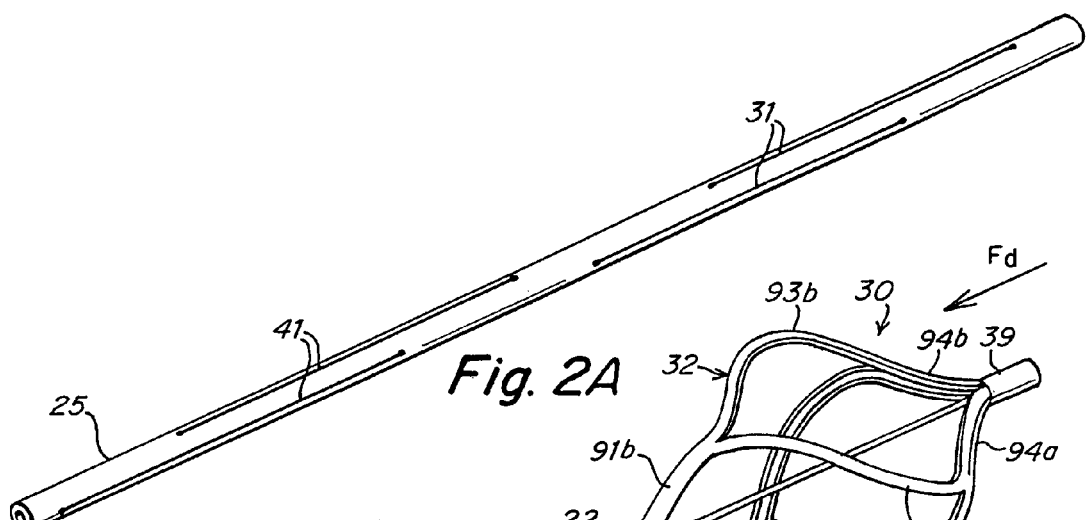
FIGS. 2A-2D are isometric views of an embodiment of an occluder according to the present invention.
Figure 2B:
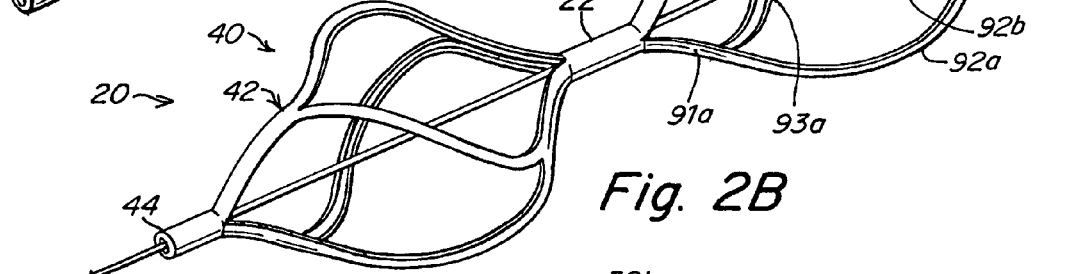
Figure 2C:
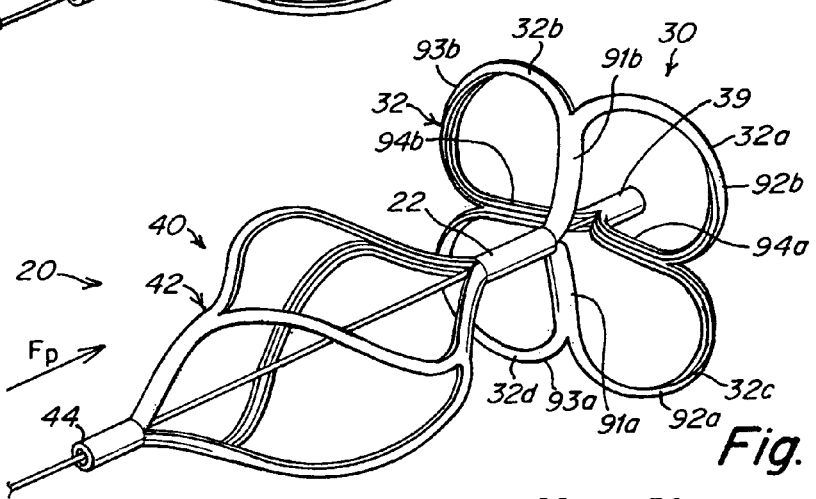
Figure 2D:
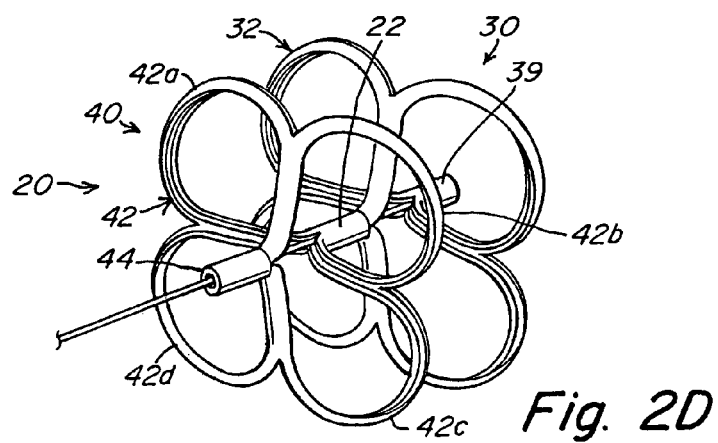
Figure 3A:
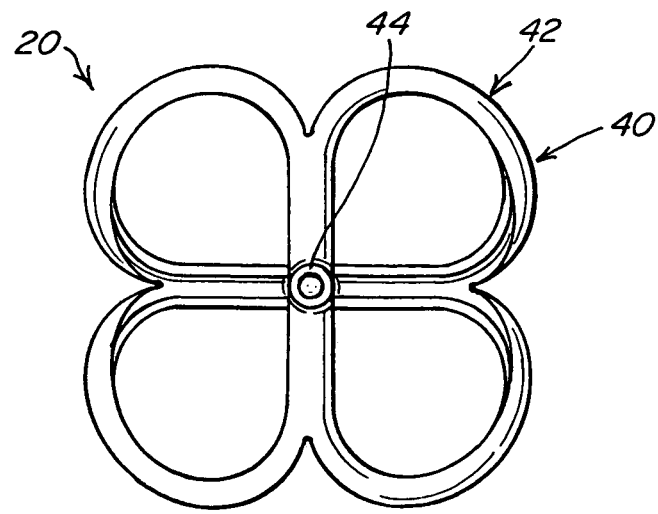
FIGS. 3A-3C are front elevational, side, and cross-sectional views, respectively, of the occluder of FIGS. 2A-2D.
Figure 3B:
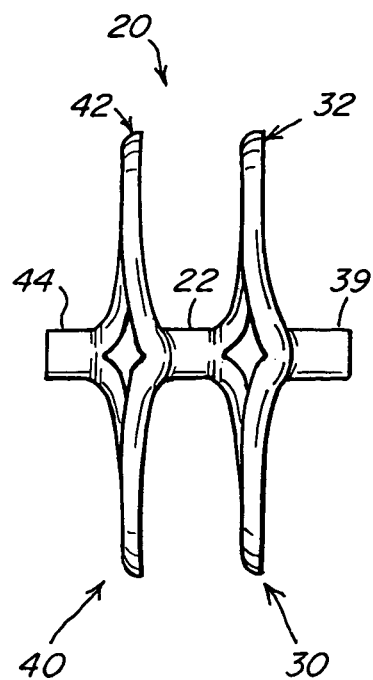
Figure 3C:
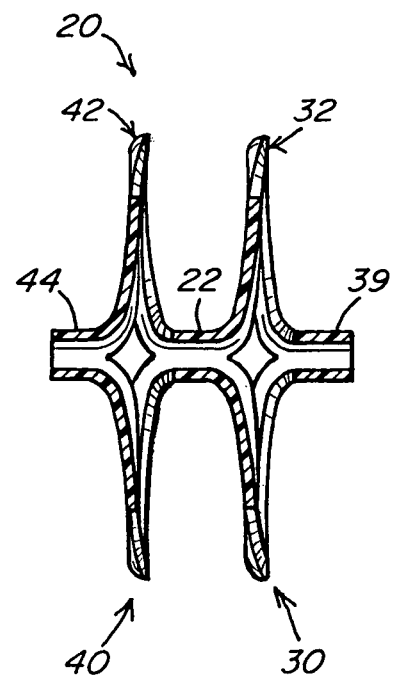

FIGS. 2D and 2H illustrate exemplary occluder 20 formed from a tube 25, according to some embodiments of the present invention. Configuration of the occluder 20 is determined by the cutting pattern on tube 25. For example, and as shown in FIGS. 2A, 2B-2D, and 3A-3C, petal-shaped loops 32, 42 (FIGS. 2A-2D and FIG. 3A) are produced by cutting slits 31 in the distal side 30 of tube 25, and cutting slits 41 in the proximal side 40 of tube 25 according to the cutting pattern shown in FIG. 2A. As shown in FIG. 2B, the distal side 30 of tube 25 is cut in half from a center portion 22 to a distal distance to form half sections 91a and 91b. The half sections 91a and 91b are further cut to a proximal distance from the distal end 39 into quarter sections 92a, 93a, 92b, and 93b. The cuts are discontinued and quarter sections 92a and 92b form half section 94a at end 39, and quarter sections 93a and 93b form half section 94b at end 39. Upon application of force $F_d$ to end 39, struts bow and twist outward to form petal-shaped loops 32 in distal side 30, as shown in FIGS. 2C-2D. The movement of the struts during deployment is such that the struts rotate in an orthogonal plane relative to the axis of the device. Central tube 22 may be constrained during the application of force $F_d$, or any combination of forces sufficient to reduce the axial length of the tube 25 may be applied. One end of each of petal-shaped loops 32 originates from central tube 22, while the other end originates from end 39 (FIGS. 2B-2C and FIG. 3A). Petal-shaped loops 42 may be formed in proximal side 40 of tube 25, as shown in FIGS. 2B-2D, using the same cutting pattern described above.

Given that the surface of occluder 20 will contact septal tissue 12 once it is deployed in vivo, slits 31 and 41 are cut so as to prevent the formation of sharp, potentially damaging edges along their length. For example, a heated cutting tool may be used to cut slits 31 and 41 such that the material of tube 25 melts slightly when placed in contact with the cutting tool. Such melting rounds the edges of the sections. Lasers may also be used to cut slits 31 and 41. According to this process, the edges of loops 32 and 42 formed by the cutting of slits 31 and 41 are blunted (due to melting) to prevent tissue damage in vivo. One skilled in the art will recognize that same considerations and techniques also apply to slits 231 and 241.

The tube(s) 25 forming occluder 20 includes a biocompatible metal or polymer. In at least some embodiments, the occluder 20 is formed of a bioabsorbable polymer, or a shape memory polymer. In other embodiments, the occluder 20 is formed of a biocompatible metal, such as a shape memory alloy (e.g., nitinol). The thermal shape memory and/or superelastic properties of shape memory polymers and alloys permit the occluder 20 to resume and maintain its intended shape in vivo despite being distorted during the delivery process. In addition, shape memory polymers and metals can be advantageous so that the structure of the device assists in compressing the PFO tunnel closed. Alternatively, or additionally, the occluder 20 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated herein by reference in their entirety.

The cross-sectional shape of tube 25 may be circular or polygonal, for example square, or hexagonal. The slits 31 and 41 (or 231 and 241) may be disposed on the face of the polygon (i.e., the flat part) or on the intersection of the faces.

The tube 25 can be extruded or constructed of a sheet of material and rolled into a tube. The sheet of material could be a single ply sheet or multiple ply. The slits that form the struts could be cut or stamped into the tube prior to rolling the tube to connect the ends to form an enclosed cross section. Various geometrical cross sections are possible including circular, square, hexagonal and octagonal and the joint could be at the vertex or along the flat of a wall if the cross section is of a particular geometry. Various attachment techniques could be used to join the ends of the sheet to form a tube, including welding, heat adhesives, non-heat adhesives and other joining techniques suitable for in-vivo application.

The surface of tube 25 may be textured or smooth. An occluder 20 having a rough surface produces an inflammatory response upon contact with septal tissue 12 in vivo, thereby promoting faster tissue ingrowth, healing, and closure of aperture 18a (shown in FIG. 1). Such a rough surface may be produced, for example, by shaving tube 25 to produce whiskers along its surface. For example, central tube 22 may include such whiskers. Additionally or alternatively, the surface of tube 25 may be porous to facilitate cell ingrowth.

The distal side 30 of the occluder 20 (also called the "anchor portion") is shown in FIGS. 2C and 2D. The distal side 30 includes four loops 32a, 32b, 32c, and 32d (collectively referred to as loops 32). As previously described, each of loops 32a-32d are formed by corresponding cut sections 92b, 93b, 92a, 93a, produced by cutting slits 31. The application of force $F_d$ to end 39 of tube 25 brings the axial ends of slits 31 together such that struts bow and twist outwardly to form loops 32 of distal side 30 (FIGS. 2B-2C). Central tube 22 may be constrained during the application of force $F_d$. One skilled in the art will recognize that any combination of forces sufficient to reduce the axial length of the tube 25 would be sufficient to deploy the distal side 30 of occluder 20.

As illustrated, the loops 32 are evenly distributed about central tube 22 and end 39. Thus, when the distal side 30 includes four loops 32 (as shown in FIGS. 2C and 2D), the four slits 31 are spaced 90 degrees radially apart. Similarly, when the distal side 30 includes six loops 32, the six slits 31 are spaced 60 degrees radially apart. The angle between radially equally-spaced is determined by the formula $(360/n_d)$, where $n_d$ is the total number of loops 32.

Although the distal side 30 of the occluder 20 shown in FIG. 3A includes four loops 32, occluders according to the present invention may include any number of loops 32 necessary for a given application. In particular embodiments, the distal side 30 of occluder 20 includes six loops 32 (FIG. 4A). Occluders having between four and ten loops 32 may be formed without requiring significant adjustments in the processes described in this application. However, occluders having less than four or more than ten loops 32 may be complicated to manufacture and difficult deliver through the vasculature.

Regardless of the number of loops included in distal side 30 and depending upon the material used to form occluder 20, the outer perimeter of loops 32 may vary. In at least some embodiments, the outer perimeter of loops 32 is rounded to provide an occluder 20 having a smooth, circular perimeter. As the number of loops 32 in the distal side 30 of occluder 20 increases, it becomes desirable to round the outer perimeters of the loops 32 so as to prevent the infliction of trauma on the surrounding septal tissue 12.

The proximal side 40 of the occluder 20, shown in side view in FIG. 2D, also includes four loops, 42a, 42b, 42c, and 42d (collectively referred to as loops 42). As previously described, each of loops 42a-42d are formed by corresponding cut sections, produced by cutting slits 41. The application of force $F_p$ to tip 44 of tube 25 brings the axial ends of slits 41 together such that struts bow and twist outwardly to form loops 42 of proximal side 40 (FIGS. 2C-2D). Central tube 22 may be constrained during the application of force $F_p$. One skilled in the art will recognize that any combination of forces sufficient to reduce the axial length of the tube 25 would be sufficient to deploy the proximal side 40 of occluder 20. As described above for distal loops 32, the loops 42 are evenly distributed about central tube 22 and tip 44. Similarly, the angle between radially equally-spaced slits 41 in the proximal side 40 is determined by the formula $(360/n_d)$, where $n_d$ is the total number of loops 42.

Although the proximal side 40 of the occluder 20 shown in FIG. 2D includes four loops 42, one skilled in the art will recognize that the proximal side 40 of an occluder according to the present invention may include any number of loops 42 required and suitable for a given application. In particular embodiments, the proximal side 40 of occluder 20 includes six loops 42 (FIG. 4A). Further, although as illustrated, distal side 30 and proximal side 40 both include four loops, there is no requirement that distal side 30 and proximal side 40 of occluder 20 include the same number of loops. In fact, in particular applications, it may be advantageous to use an occluder 20 in which the distal side 30 contains fewer loops than the proximal side 40, or vice versa.

It will be apparent to one skilled in the art that loops 32 and loops 42 (or loops 232 and 242) do not have to be the same size. In one embodiment, loops 32 (or 232) are larger in size than loops 42 (or 242). In another embodiment, loops 32 (or 232) are smaller in size than loops 42 (or 242). Size of loops 32 and 42 (or 232 and 242) is determined by the lengths of slits 31 and 41 (or 231 and 241), respectively. Therefore, absolute and relative lengths of slits 31 and 41 (or 232 and 241) can be varied to achieve desired absolute and relative sizes of loops 32 and 42 (or 232 and 242).

In at least some embodiments, illustrated in FIG. 4A, loops 42 of the proximal side 40 are radially offset from loops 32 of the distal side 30 to provide a better distribution of forces around the aperture 18a. This can be achieved by making cuts to create slits 31 and 41 such that they are radially offset relative to each other. The maximum degree of offset will depend on the number of slits. In general, if slits are equally spaced, the maximum possible offset will be one half of the angle between the loops. For example, if distal side 30 (or proximal side 40) contains 4 slits (and therefore 4 loops), loops will be 90 degrees apart (see the formula described above), thereby allowing for maximum degree of offset of one half of 90 degrees (which is 45 degrees) between loops 32 and loops 42. In a preferred form, when distal side 30 (or proximal side 40) contains 4 slits (and therefore 4 loops), loops 42 and loops 32 are offset by 45 degrees. In an alternative embodiment, the degree of offset between loops 32 and 42 ranges from about 30 to about 45 degrees.

FIGS. 2E-2H illustrate another embodiment of the invention, where the occluder 20 is formed from a tube with loops 232 and 242, produced from the cutting pattern shown in FIG. 2E. In one embodiment, the proximal side 40 and the distal side 30 of occluder 20 each include eight loops or petals. As shown in FIG. 2E, the distal portion 30 of the tube 25 includes 8 slits 231 that form 8 extended segments of the tube that form the distal loops or petals 232. As apparent from the figures, the slits extend the entire distance of the distal portion 30 of the tube 25, i.e. between central tube 22 and distal end 39, so that the loops of identical cross-sections are formed. Upon application of force F.sub.d to distal end 39, extended segments defined by slits 231 bow and twist outward to form distal petals 232 in distal side 30 of the occluder 20. The movement of the segments during deployment is such that the segments rotate in an orthogonal plane relative to the axis of the device. Central tube 22 may be constrained during the application of force F.sub.d, or any combination of forces sufficient to reduce the axial length of the tube may be applied. One end of each of distal petals 232 originates from central tube 22, while the other end originates from distal end 39. Proximal petals 242 may be formed in proximal portion 40, as shown in FIGS. 2E-2H, making slits 241 between central tube 22 and proximal tip 44, using the same cutting pattern described above and applying force F.sub.p or combination of forces sufficient to reduce the axial length of the tube by allowing slits 241 to bow and twist outward to form proximal petals 242 in proximal portion 40 of the occluder 20. One end of each of proximal petals 242 originates from central tube 22, while the other end originates from proximal tip 44. A catch system may take a variety of forms, further non-limiting examples of which are provided below in FIGS. 6A-6E. For example, as shown in FIGS. 2F and 2H, the catch system includes two catch elements, e.g., ball 133 and flange 135', operatively connected to delivery string 137.

One embodiment of the distal side 30 of the occluder 20 (also called the "anchor portion") is shown in FIGS. 2G and 2H. The distal side 30 includes eight loops 232a, 232b, 232c, 232d, 232e, 323f, 232g, and 232h (collectively referred to as loops 232). As previously described, each of loops 232a-232h is produced by cutting slits 231. The application of force $F_d$ to end 39 of tube 25 brings the axial ends of slits 231 together such that struts bow and/or twist outwardly to form loops 232 of distal side 30 (FIGS. 2F-2G). Central tube 22 may be constrained during the application of force $F_d$. One skilled in the art will recognize that any combination of forces sufficient to reduce the axial length of the tube 25 would be sufficient to deploy the distal side 30 of occluder 20.

As illustrated, the loops 232 are evenly distributed about central tube 22 and end 39. Thus, when proximal side 30 includes eight loops 232 (as shown in FIGS. 2G and 2H), the eight slits 231 are spaced 45 degrees radially apart. The angle between radially equally-spaced slits 231 in distal side 30 is determined by the formula $(360/n_d)$ where $n_d$ is the total number of loops 232.

The proximal side 40 of the occluder 20, shown in side view in FIG. 2H, also includes eight loops, 242a, 242b, 242c, 242d, 242e, 242f, 242g, and 242h (collectively referred to as loops 242). As previously described, each of loops 242a-242h is produced by cutting slits 241. The application of force $F_p$ to tip 44 of tube 25 brings the axial ends of slits 241 together such that struts bow and twist outwardly to form loops 242 of proximal side 40 (FIGS. 2G-2H). Central tube 22 may be constrained during the application of force $F_p$. One skilled in the art will recognize that any combination of forces sufficient to reduce the axial length of the tube 25 would be sufficient to deploy the proximal side 40 of occluder 20. As described above for distal side 30, the loops 242 are evenly distributed about central tube 22 and tip 44. Similarly, the angle between radially equally-spaced slits 241 in proximal side 40 is determined by the formula $(360/n_d)$ where $n_d$ is the total number of loops 242.

Although the distal side 30 and the proximal side 40 of the occluder 20, shown in FIG. 2H, each include eight loops 232 and 242, respectively, one skilled in the art will recognize that the distal side 30 and proximal side 40 of an occluder 20 according to the present invention may include any number of loops 232 and 242, respectively, required and/or suitable for a given application. Further, although as illustrated, distal side 30 and proximal side 40 both include eight loops, there is no requirement that distal side 30 and proximal side 40 include the same number of loops. In fact, in particular applications, it may be advantageous to use an occluder 20 in which distal side 30 contains fewer loops than proximal side 40, or vice versa.

It will be apparent to one skilled in the art that loops 232 and loops 242 do not have to be the same size. In one embodiment, loops 232 are larger in size than loops 242. In another embodiment, loops 232 are smaller in size than loops 242. Size of loops 232 and 242 is determined by the lengths of slits 231 and 241, respectively. Therefore, absolute and relative lengths of slits 231 and 241 can be varied to achieve desired absolute and relative sizes of loops 232 and 242.

While loops 232 and 242, shown in FIGS. 2F-2H are illustrated as aligned, this does not have to be the case. In one embodiment, loops 232 and 242 are radially offset from each other. This can be achieved by making cuts to create slits 231 and 241 such that they are radially offset relative to each other. The maximum degree of offset will depend on the number of slits. In general, if slits are equally spaced, the maximum possible offset will be one half of the angle between the loops. For example, if distal side 30 (or proximal side 40) contains 8 slits (and therefore 8 loops), the loops will be 45 degrees apart (see the formula described above), thereby allowing for maximum degree of offset of one half of 45 degrees, which is 22.5 degrees between loops 232 and loops 242. It is understood, that offset can be in either rotational direction (i.e., clockwise and counterclockwise). Therefore, in this example with 8 slits, an offset of 30 degrees is equivalent to an offset of 7.5 degrees in the opposite direction.

The cutting pattern illustrated in FIG. 2E can be varied, as shown in FIGS. 2I-2K. According to one embodiment of the invention, the number of slits 231 and 241 cut in the tube 25 can be changed according to the desired number of loops 232 and 242 in the occluder 20 when deployed. The cross-sectional dimensions of loops 232 and 242 are determined by the thickness of tube 25 and the distance between adjacent slits 231 and 241. The length of slits 231 and 241 determines the length of loops 232 and 242 and the radial dimensions of the deployed occluder 20. In this manner, the dimensions of loops 232 and 242 can be controlled during production of occluder 20. For example, as more material is removed from tube 25 during the cutting process used to form slits 231 and 241, the thickness of loops 232 and 242 decreases. Moreover, any or all of slits 231 and 241 can be cut such that thickness of loops 232 and 242 varies along their length. In some embodiments, it may be desirable to have wider loops 232 and 242 at the location where the loops join tube 25 to create a sturdier device. Alternatively, it may be desirable to have a wider portion elsewhere along the loops 232 and 242 such that occluder 20 is predisposed to bend into a certain shape and arrangement. For example, the portion of loops 232 and 242 nearer central tube 22 may be thinner than the portion of loops 232 and 242 nearer end 39 and tip 44, respectively, to facilitate bending of the loops 232 and 242.

Slits 231 and 241, as shown in FIG. 2J, are cut axially along the length of tube 25. However, as one of skill in the art will recognize, slits 231 and/or 241 may also be cut along other dimensions of tube 25. For example, as shown in FIG. 2I, slits 231 and 241 may be cut at an angle such that they are helically disposed on tube 25. Angled slits 231 and 241 produce angled loops 232 and 242 during deployment. Further, slits 231 and 241 need not be straight; for example, slits 231 and 241 may be cut as zigzags, S-shaped slits, or C-shaped slits. One skilled in the art will be capable of selecting the angle for the slits 231 and/or 241 and the loop 232 and 242 shape(s) appropriate for a given clinical application. For example, when occluder 20 is formed from a polymer tube 25, straight loops 232 and 242 may be preferable because they will impart maximum stiffness to occluder 20. If the tube 25 is formed of a stiffer material, the angled slits 231 and/or 241 may provide a more desired stiffness to the occluder 20.

In one embodiment, the occluder 20 has loops according to FIGS. 2A-2D on one side and loops according to FIGS. 2E-2H on the other side. For example, occluder 20 may comprise loops 42 on the proximal side 40 and loops 232 on the distal side 30, or it may comprise loops 242 on the proximal side 40 and loops 32 on the distal side 30.

In one embodiment, for example as shown in FIG. 2H, each loop 242 and 232 has some amount of twist, i.e., when the loop is formed, the proximal side of the loop is radially offset with respect to the distal side of the loop. Loops 242 and/or 232, however, need not have any twist.

FIG. 2M, for example, illustrates an embodiment of the occluder with slits cut as illustrated in FIG. 2L. In this embodiment, neither loops 32 nor loops 42 are twisted. It will be apparent to one skilled in the art that any combination of twisted and untwisted loops may be used. Furthermore, an occluder can have any combination of loops with different bends and twists if desired.

In one embodiment, loops 32 (or 232) of distal side 30 are bent to form concave loops, while loops 42 (or 242) of proximal side 40 are flat (FIG. 11). In this embodiment, the outermost portions of loops 42 (or 242) of proximal side 40 oppose the outermost portions of the loops 32 (or 232) of the proximal side 30, as described in more detail below, thereby creating a desirable opposing force that secures the occluder 20 at its desired location in vivo. So configured, the opposing compressive forces exerted by sides 30 and 40 on the septal tissue 12 following deployment of occluder 20 in vivo is advantageous in certain circumstances, such as closing certain kinds of PFOs. In another embodiment, loops 42 (or 242 of the proximal side 40 are bent, while loops 32 (or 232) of the distal side 30 are flat. In yet another embodiment, loops 42 (or 242) of the proximal side 40 and loops 32 (or 232) of the distal side 30 are bent.

Whatever the number and shapes of loops 32 and 42 (or 232 and 242), the loops 32 and 42 (or 232 and 242) may be of varied sizes to facilitate delivery of occluder 20, e.g. to improve collapsibility of the occluder 20 or to enhance its securement at the delivery site. For example, loops 32 and 42 (or 232 and 242) that are sized to better conform with anatomical landmarks enhance securement of the occluder 20 to the septal tissue 12 in vivo. As indicated above, the cross-sectional dimensions of loops 32 and 42 (or 232 and 242) are determined by the thickness of tube 25 and the distance between adjacent slits 31 and 41 (or 231 and 241). The length of slits 31 and 41 (or 231 and 241) determines the size of loops 32 and 42 (or 232 and 242) and the radial extent of the deployed occluder 20. In at least some embodiments, each of distal side 30 and proximal side 40 has a diameter in the range of about 10 mm to about 45 mm, with the particular diameter determined by the size of the particular defect being treated. In particular embodiments, the diameter of distal side 30 will be different than that of proximal side 40 so as to better conform to the anatomy of the patient's heart.

According to one embodiment of the invention, the loops of the occluder are formed by struts as illustrated in FIG. 2B. Sections 91a, 91b, 92a, 92b, 93a, 93b, 94a, and 94b are of equal distance, being about ⅓ the length of distal side 30 (i.e., the distance between central tube 22 and end 39) of the tube 25. According to another embodiment of the invention, other lengths of sections can be used to produce advantageous results. In general, the longer the length of the hemispherical struts, such as half sections 91a, 91b, 94a, and 94b, the stiffer the occluder will be. The longer the length of the quarter (as shown) struts, such as half sections 92a, 92b, 93a, and 93b, the less stiff the occluder will be. In general, the hemispherical cut (one of the two) may be 20-40% of the overall length of the distal side (or proximal side) the tube. Specifically, the hemispherical cuts could be 40% of the overall length of the distal side (or proximal side) and then the quarter cut could be 20% of the overall length of the distal side (or proximal side) of the tube 25. Also, the lengths of the hemispherical cuts need not be the same. It may be advantageous to shorten one or the other side of the hemispherical cut based on a desired stiffness characteristic for a particular application of the occluder. In an alternative structure, the hemispherical cuts can be extended in a range up to 100% of the length of the distal side (or the proximal side) of the occluder, while still enabling the bow and twist of the struts.

As indicated previously and shown in FIGS. 2A-2H, distal side 30 and proximal side 40 of occluder 20 are connected by central tube 22. The central tube 22 is formed by the portion of tube 25 between the distal side 30 of tube 25, which contains slits 31, (or 231) and the proximal side 40 of tube 25, which contains slits 41 (or 241). Given that the central portion of tube 25 remains uncut during the cutting process, the central portion of the tube maintains its profile upon the application of forces $F_d$ and $F_p$ and does not bow and twist outward as the proximal and distal sides are adapted to do.

According to one embodiment, central tube 22 is straight, as illustrated in FIGS. 2D and 2H, where the central tube 22 is perpendicular to loops 32 and 42 (or 232 and 242). According to another embodiment of the invention, central tube 22 is positioned at an angle θ relative to the proximal side 40 of the occluder 20, as shown, for example, in FIGS. 5B and 11. The shape of central tube 22 included in a given occluder is, at least in part, determined by the nature of the aperture 18. An occluder having a straight central tube 22 is particularly suited to treat an anatomical anomaly including a perpendicular aperture, such as an ASD and certain PFOs. Often, however, anatomical anomalies, such as certain PFOs, have non-perpendicular apertures and are sometimes quite significantly non-perpendicular. An occluder having an angled central tube 22 is well-suited for treatment of such defects, such that the angle of the anatomical aperture 18 is more closely matched by the pre-formed angle θ of the occluder 20. Also, the length of central tube 22 can be varied depending on the anatomy of the defect being closed. Accordingly, the distal side 30 and proximal side 40 of occluder 20 are more likely to be seated against and minimize distortion to the septal tissue 12 surrounding the aperture 18, as shown in FIG. 13. A well-seated occluder 20 is less likely to permit blood leakage between the right 11 and left 13 atria, and the patient into which the occluder 20 has been placed is, therefore, less likely to suffer embolisms and other adverse events.

Advantageously, angled central tube 22 also facilitates delivery of occluder 20 because it is angled toward the end of the delivery sheath. In at least some embodiments, the angle θ is about 0-45 degrees. To form the angle θ, proximal side 40 of the occluder 20 bends depending upon, among other factors, the material used to form occluder 20. Accordingly, depending upon design considerations, tip 44 and end 39 may be aligned with central tube 22 or perpendicular to proximal side 40 or some variation in between. One skilled in the art will be capable of determining whether a straight or angled central tube 22 is best suited for treatment of a given anatomical aperture 18 and the appropriate angle θ, typically in the range between about 30 and about 90 degrees. Sometimes, angles of about 0 degrees to about 30 degrees can be used in an oblique passageway such as a very long tunnel PFO. One skilled in the art will recognize that the concept of an angled central tube may be applied to septal occluders other than those disclosed herein.

When central tube 22 is positioned at angle θ, distal side 30 and proximal side 40 of occluder 20 may be configured such that they are either directly opposing or, as shown in FIGS. 5B, 11 and 12, offset by distance A. One skilled in the art will, of course, recognize that the shape and arrangement of either or both of distal side 30 and proximal side 40 may be adjusted such that the compressive forces they apply are as directly opposing as possible. However, in some clinical applications, an occluder 20 having an offset of distance A may be particularly desirable. For example, as shown in FIGS. 5B, and 11-12, if the septal tissue 12 surrounding aperture 18 includes a disproportionately thick portion (e.g. septum secundum 16 as compared to septum primum 14), the offset A may be used to seat occluder 20 more securely upon septal tissue 12. Moreover, the offset A allows each of sides 30 and 40 to be centered around each side of an asymmetric aperture 18.

When a central tube 22 at angle θ is included in occluder 20, a marker is required to properly orient the occluder 20 in its intended in vivo delivery location. For example, a platinum wire may be wrapped around one of loops 32 or 42 (or one of loops 232 or 242) so as to permit visualization of the orientation of the occluder 20 using fluoroscopy. Alternatively, other types of markers may be used, e.g. coatings, clips, etc. As one skilled in the art would appreciate, the radiopaque marker could be blended in with the extrudate and thus provide visibility under fluoroscopy. As will be readily understood by one skilled in the art, the orientation of a non-symmetrical occluder 20 during delivery is of great importance. Of course, when a non-symmetrical occluder 20 is used, the periphery of the occluder 20 may be configured such that the clamping force applied by the proximal side 40 is directly opposed to that applied by the distal side 30.

Upon deployment in vivo (a process described in detail below), an occluder 20 according to the present invention applies a compressive force to the septal tissue 12. Distal side 30 is seated against the septal tissue 12 in the left atrium 13, central tube 22 extends through the aperture 18, and proximal side 40 is seated against the septal tissue 12 in the right atrium 11. At least some portion of each of loops 32 and 42 (or 232 and 242) contacts septal tissue 12. In particular embodiments, a substantial length of each of loops 32 and 42 (or 232 and 242) contacts septal tissue 12. As illustrated in the representative Figures, the proximal side 40 and distal side 30 of occluder 20 overlap significantly, such that the septal tissue 12 is "sandwiched" between them once the occluder 20 is deployed. According to at least some embodiments and depending upon the material used to form occluder 20, the loops 32 and 42 (or 232 and 242) provide both a radially-extending compressive force and a circumferential compressive force to septal tissue 12. In these embodiments, the compressive forces are more evenly and more widely distributed across the surface of the septal tissue 12 surrounding the aperture 18 and, therefore, provide the occluder 20 with superior dislodgement resistance as compared to prior art devices. As used in this application, "dislodgement resistance" refers to the ability of an occluder 20 to resist the tendency of the force applied by the unequal pressures between the right 11 and left 13 atria (i.e. the "dislodging force") to separate the occluder 20 from the septal tissue 12. Generally, a high dislodgement resistance is desirable.

Loops 32 and 42 (or 232 and 242) are also configured to minimize the trauma they inflict on the septal tissue 12 surrounding aperture 18. Specifically, as indicated previously, the outer perimeter of loops 32 and 42 (or 232 and 242) may be rounded.

According to one embodiment of the invention, for example, as illustrated in FIGS. 2B-2D, the circumferential portions of loops 32 and 42 are thinner than the orthogonally-extending portions of loops 32 and 42; therefore, the center of the occluder 20 is stronger than its perimeter. Accordingly, outer perimeter of loops 32 and 42 of occluder 20 has a low compression resistance. As used in this application, "compression resistance" refers to the ability of an occluder 20 to resist the lateral compressive force applied by the heart as it contracts during a heartbeat. Generally, an occluder that resists compressive force, i.e. has high compression resistance, is undesirable because its rigid shape and arrangement may cause trauma to the septal tissue 12, the right atrium 11, and/or the left atrium 13.

According to at least some embodiments of the present invention, occluder 20 further includes a catch system, generally indicated at 131, that secures the occluder 20 in its deployed state. The catch system 131, in general, maintains the shape and arrangement of loops 32 and 42 (or 232 and 242) of occluder 20, once the occluder 20 has been deployed. Catch system 131 reduces and maintains the axial length of the occluder 20 so that occluder 20 maintains its deployed state, is secured in the aperture 18, and consistently applies a compressive force to septal tissue 12 that is sufficient to close aperture 18. Catch system 131 is particularly advantageous when the occluder 20 is formed of a polymeric material, as previously described, because the polymeric occluder 20 may be deformed during delivery such that it may not fully recover its intended shape once deployed. By reducing and maintaining the axial length of occluder 20 once it has been deployed in vivo, catch system 131 compensates for any undesirable structural changes suffered by occluder 20 during delivery. In some embodiments, catch system 131 includes a ceramic material or a material selected from the group consisting of metals, shape memory materials, alloys, polymers, bioabsorbable polymers, and combinations thereof. In particular embodiments, the catch system may include nitinol or a shape memory polymer. Further, the catch system may include a material selected from the group consisting Teflon-based materials, polyurethanes, metals, polyvinyl alcohol (PVA), extracellular matrix (ECM) or other bioengineered materials, synthetic bioabsorbable polymeric scaffolds, collagen, and combinations thereof.

Figure 6A:
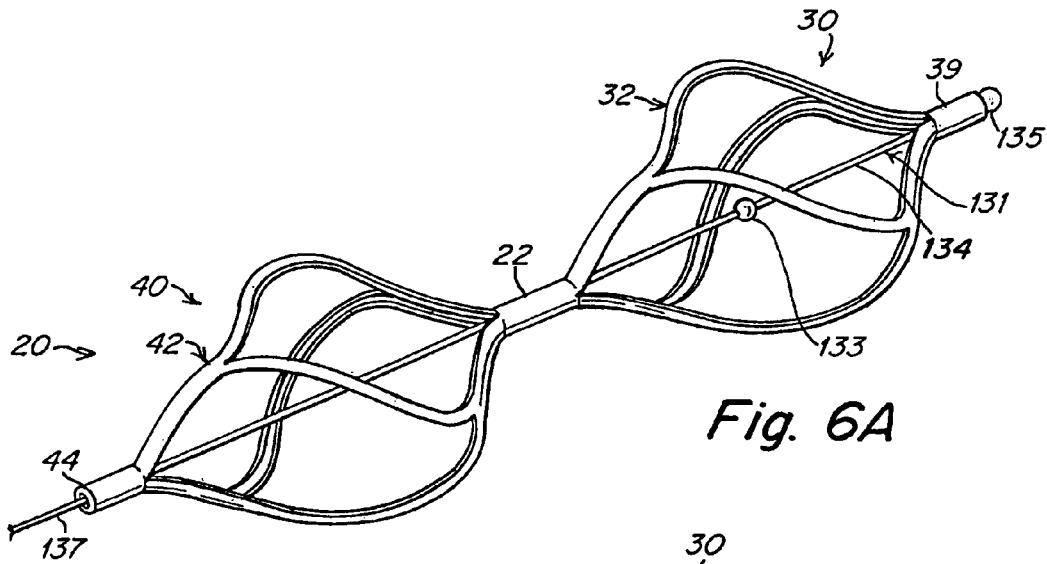
FIGS. 6A-6E are isometric views of one embodiment of a catch system according to the present invention.
Figure 6B:
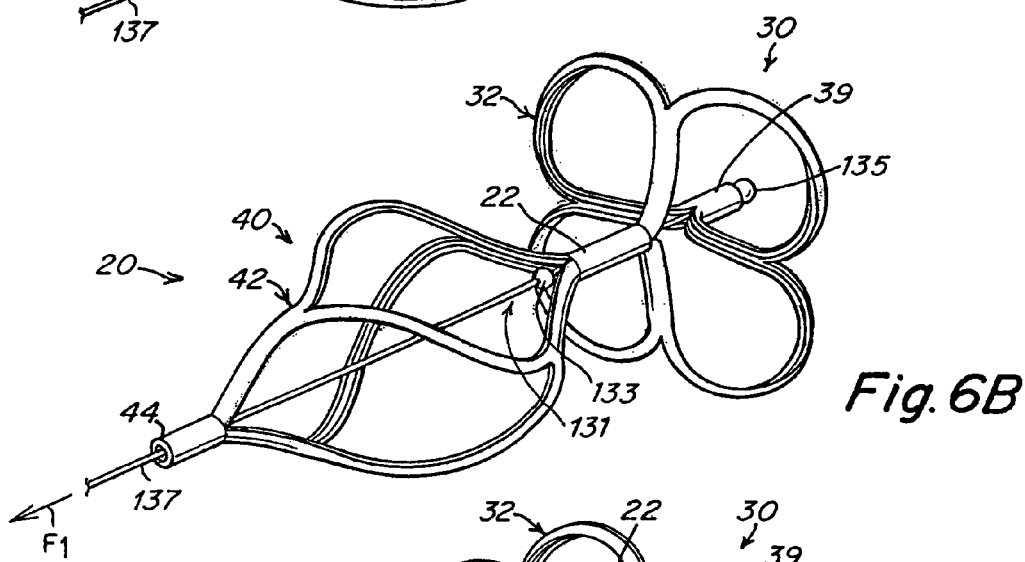
Figure 6C:
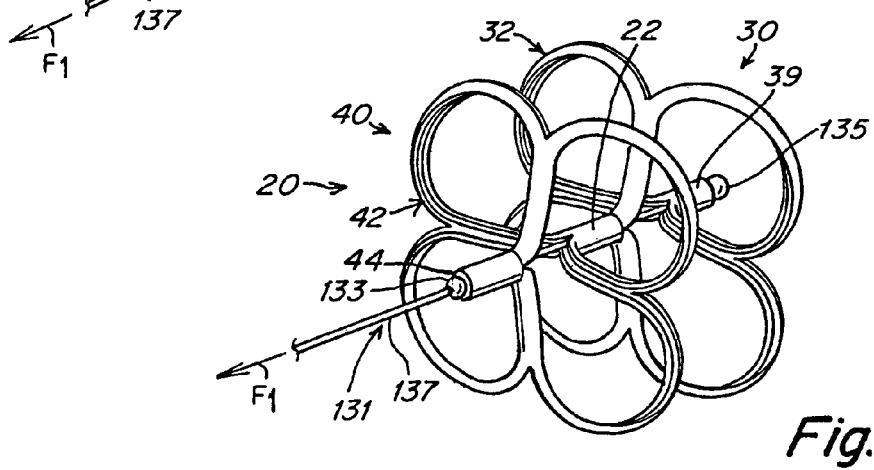
Figure 6D:
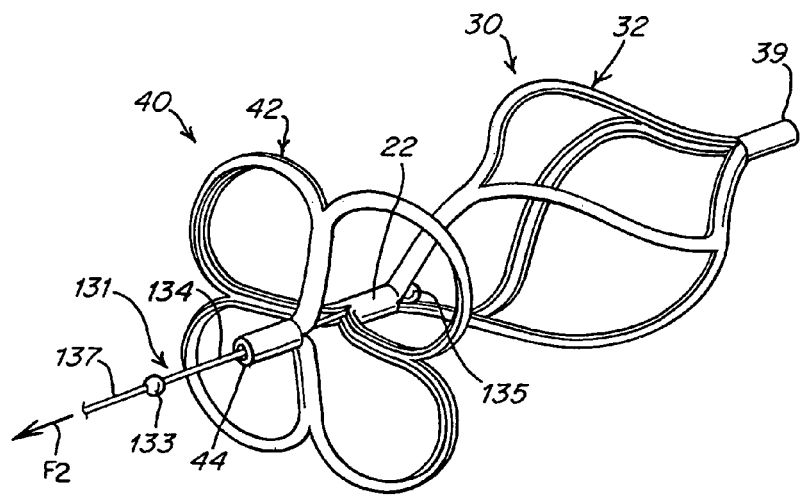
Figure 6E:
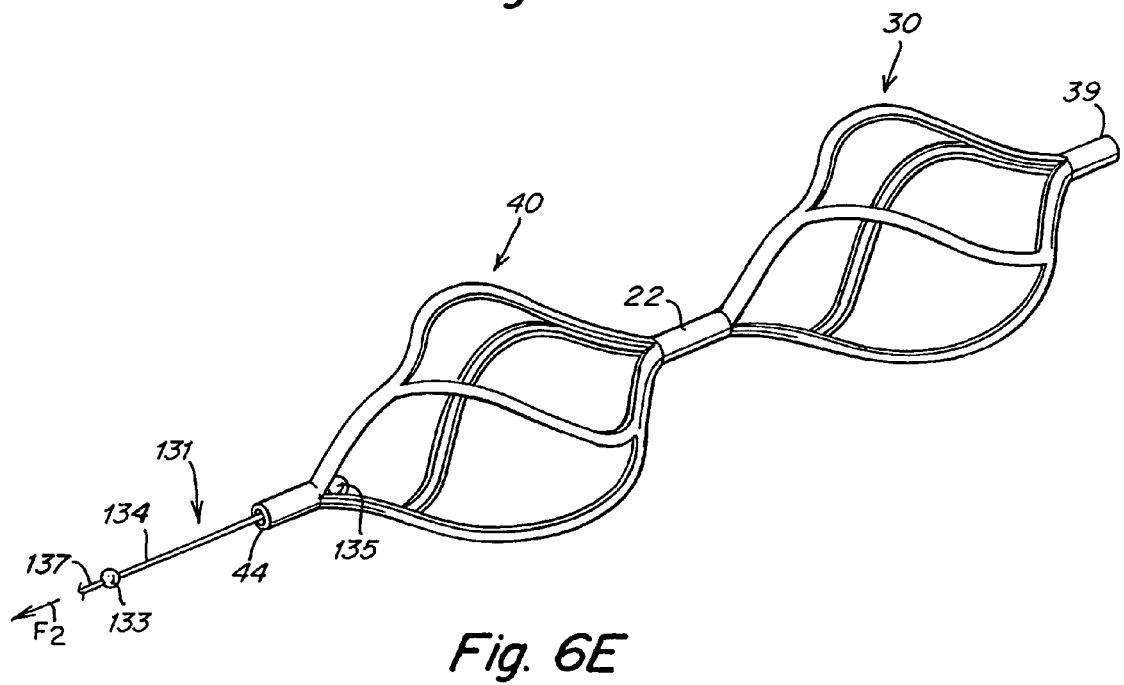

Catch system 131 may take a variety of forms, non-limiting examples of which are provided in FIGS. 6A-6E. For example, as shown in FIG. 6A, catch system 131 includes two catch elements, e.g., balls, 133 and 135, connected by wire 134. The catch system and catch element are preferably made of the same material as the occluder, although based on design selection, they could be made of the same or different material. In certain circumstances, it may be necessary to make them of different material. As illustrated in FIG. 6A, delivery string 137 is attached to ball 133 and is then extended through end 39, distal portion 30 of tube 25, central tube 22, proximal portion 40 of tube 25, and tip 44, such that ball 133 is located between central tube 22 and end 39 and ball 135 is located on the distal side of central tube 22. The function of catch system 131 is shown in FIGS. 6B-6E. Ball 133 is designed such that, upon the application of sufficient pulling force $F_1$ to delivery string 137, it passes through central tube 22 (FIG. 6B) and tip 44 (FIG. 6C). Ball 133 cannot reenter tip 44 or central tube 22 without the application of a sufficient, additional force. In this manner, ball 133 may be used to bring together the distal side 30 and the proximal side 40, thereby reducing and maintaining the axial length of occluder 20. Obviously, during the application of pulling force $F_1$, the tip 44 of occluder 20 must be held against an object, such as a delivery sheath. Ball 135 is designed such that, upon application of sufficient pulling force $F_2$ to delivery string 137, it passes through end 39 (FIG. 6D) and central tube 22 (FIG. 6E). The pulling force $F_2$ required to move ball 135 through end 39 and central tube 22 is greater than the pulling force $F_1$ required to move ball 133 through central tube 22 and tip 44. However, ball 135 cannot pass through tip 44. Thus, the application of sufficient pulling force $F_2$ to ball 135 releases distal side 30 and proximal side 40, as described in more detail below. It should be noted that while catch elements 133 and 135 are illustrated as spherical elements in FIGS. 6A-6E, catch elements 133 and 135 may take any suitable shape. For example, catch elements 133 and 135 may be conical. The narrow portions of conical catch elements 133 and 135 point toward tip 44 of proximal side 40. One possible mode of recovery or retrieval for this device is simply reversing the implantation procedure. Of course, other modes of recovery or retrieval are possible, some of which are described in this specification.

Figure 7A:
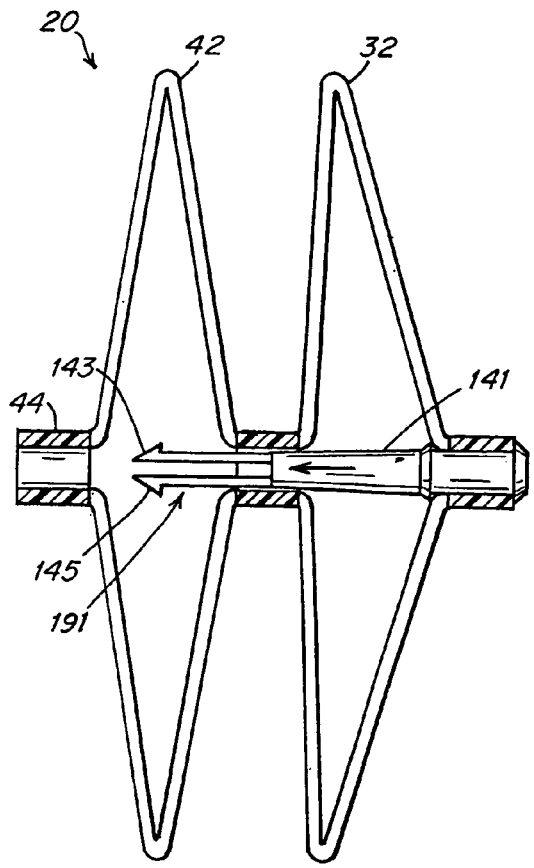
FIGS. 7A-7C are side views of another embodiment of a locking mechanism according to the present invention.
Figure 7B:
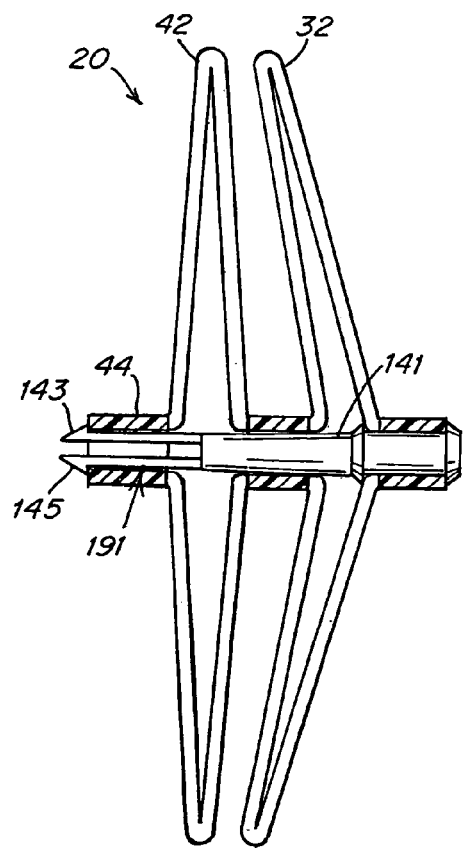
Figure 7C:
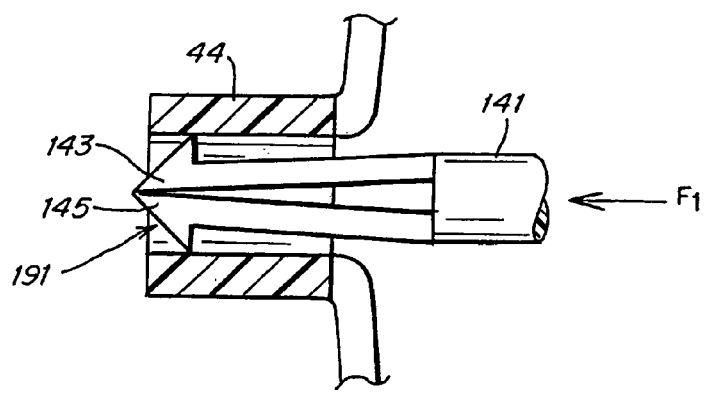

A different system for securing the device in the deployed state is shown in FIGS. 7A-7C. A locking mechanism 191 includes a hollow cylinder 141 having at least two half-arrows 143 and 145 located at its proximal end (FIG. 7A). Cylinder 141 enters tip 44 under application of pulling force $F_1$ to delivery string 137. As cylinder 141 enters tip 44, half-arrows 143 and 145 are forced together such that the diameter of the proximal end of cylinder 141 is reduced (FIG. 7C). Under continued application of pulling force $F_1$, half-arrows 143 and 145 pass through tip 44 and expand to their original shape and arrangement (FIG. 7B). Given that half-arrows 143 and 145 extend beyond the diameter of tip 44, the axial length of an occluder 20 including the locking mechanism 191 shown in FIGS. 7A-7C is maintained in its reduced state. If the implant needs to be removed or repositioned, the locking mechanism 191 shown in FIGS. 7A-7C may be released by moving half-arrows 143 and 145 together such that the diameter of the proximal end of cylinder 141 is smaller than that of tip 44 and cylinder 141 passes through tip 44. Cylinder 141 may then be withdrawn from tip 44.

One skilled in the art will recognize that catch system 131 may assume numerous configurations while retaining its capability to reduce and maintain the axial length of occluder 20 such that occluder 20 maintains its deployed state. For example, catch system 131 may include a threaded screw, a tie-wrap, or a combination of catch systems 131. Furthermore, catch system 131 may include multiple members that may provide a stepped deployment process. For example, catch system 131 as depicted in FIGS. 6A-6E may include three balls. In this configuration, one ball is used to secure the distal end 30 of occluder 20 and another ball is used to secure the proximal end 40 of occluder 20, and the third ball is secured to the distal end. Any suitable catch system 131 may be incorporated into any of the embodiments of occluder 20 described herein. One skilled in the art will be capable of selecting the catch system 131 suitable for use in a given clinical application.

Occluder 20 may be modified in various ways. According to some embodiments of the present invention, distal side 30 and/or proximal 40 side of occluder 20 may include a tissue scaffold. The tissue scaffold ensures more complete coverage of aperture 18 and promotes encapsulation and endothelialization of septal tissue 12, thereby further encouraging anatomical closure of the septal tissue 12. The tissue scaffold may be formed of any flexible, biocompatible material capable of promoting tissue growth, including but not limited to polyester fabrics, Teflon-based materials, ePTFE, polyurethanes, metallic materials, polyvinyl alcohol (PVA), extracellular matrix (ECM) or other bioengineered materials, synthetic bioabsorbable polymeric scaffolds, other natural materials (e.g. collagen), or combinations of the foregoing materials. For example, the tissue scaffold may be formed of a thin metallic film or foil, e.g. a nitinol film or foil, as described in United States Patent Publ. No. 2003/0059640 (the entirety of which is incorporated herein by reference). In those embodiments, where occluder 20 includes a tissue scaffold, the scaffold may be located on the outside the face of distal side 30 and proximal side 40 of the occluder, with an alternative of including scaffold also inside the face of distal side 30 and proximal side 40 of the occluder. Also, the tissue scaffold could be disposed against the tissue that is sought to be occluded, such as the septal tissue 12 so that the proximity of the tissue scaffold and septal tissue 12 promotes endothelialization. Loops 32 and 42, (or 232 and 242), can be laser welded, ultrasonically welded, thermally welded, glued, or stitched to the tissue scaffold to securely fasten the scaffold to occluder 20. One skilled in the art will be able to determine those clinical applications in which the use of tissue scaffolds and/or stitches is appropriate.

Figure 8A:
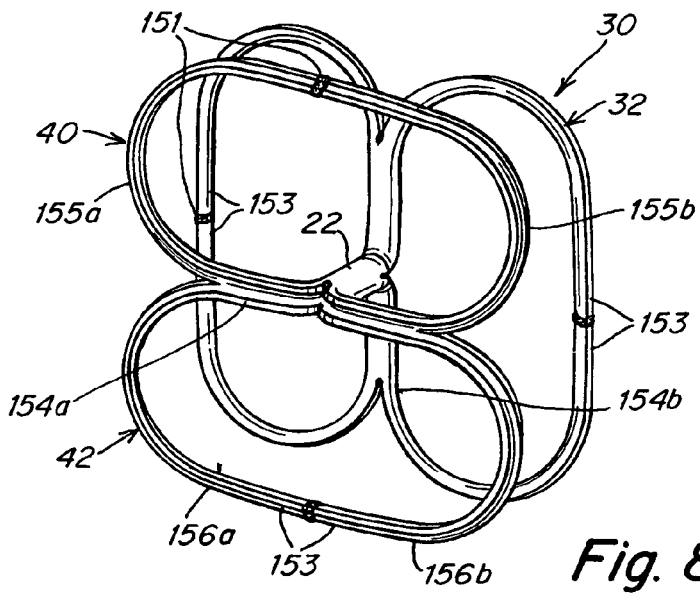
FIGS. 8A-8C are isometric views of yet another embodiment of an occluder according to the present invention.
Figure 8B:
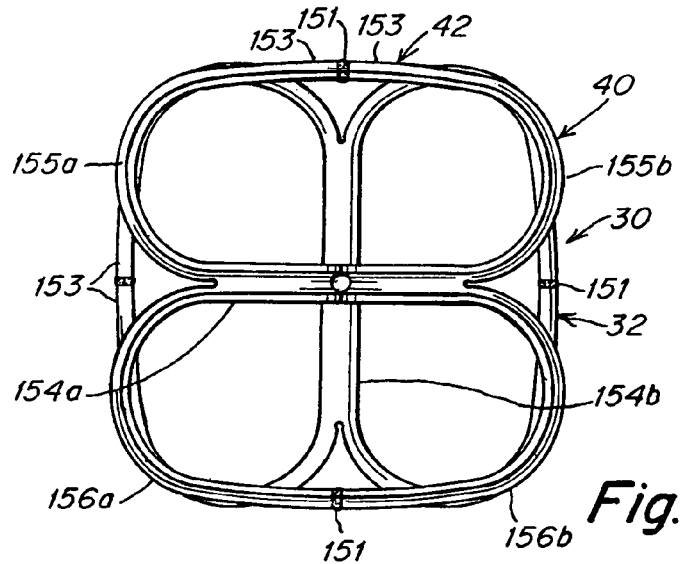
Figure 8C:
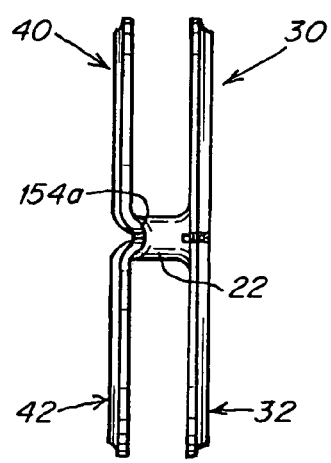

Occluder 20 may be further modified so that it lacks end 39 and tip 44, as shown in FIGS. 8A-8C, and, therefore, has a reduced septal profile. Such an occluder may be formed in several ways. For example, according to one embodiment, slits 31 and 41 are extended through end 39 and tip 44, respectively, of tube 25 during the cutting process. This cutting pattern produces struts 32 that deform during deployment to produce incomplete loops 32. One side of the device, facing the viewer as shown in FIG. 8A, is formed by slits 31 that extend along the tube 25 to varying lengths. The tube 25 is cut in half to form half sections 154a and 154b. The half sections 154a and 154b are further cut to a proximal distance from the end 39 into quarter sections 155a, 156a, 155b, and 156b. The ends of the quarter sections 155a and 155b are joined at "free ends" 153 to close the loop 32. Similarly, the free ends of quarter sections 156a and 156b may be joined by appropriate cutting, see FIG. 8b. The ends may be joined using any suitable connectors, e.g., 151, e.g., welds. One of skill in the art will recognize that the free ends 153 of loops 32 may be connected using other means, including but not limited to seams and bonds obtained by heat or vibration.

In the above embodiment, the slits in the quarter sections are run completely through the end of the tube 39. In an alternative embodiment, the end 39 may remain uncut, thereby eliminating the need for a weld to join the quarter sections together.

The embodiment illustrated in FIGS. 8A-8C depicts an occluder 20 in which both sides are formed according to the above-described design. Alternatively, an occluder 20 according to the present invention may include a hybrid structure, wherein one side is designed according to the embodiment shown in FIGS. 8A-8C and the other side is designed according to other types of structures disclosed in this application.

Occluder 20 may be prepared for delivery to an aperture 18 in any one of several ways. Slits 31 and 41 (or 231 and 241) may be cut such that tube 25 bends into its intended configuration following deployment in vivo. Specifically, slits 31 and 41 (or 231 and 241) may be cut to a thickness that facilitates the bending and formation of loops 32 and 42 (or 232 and 242). Upon the application of forces $F_d$ and $F_p$, tube 25 bends into its intended deployed configuration. Alternatively and/or additionally, tube 25 formed of a shape memory material may be preformed into its intended configuration ex vivo so that it will recover its preformed shape once deployed in vivo. According to at least some embodiments, these preforming techniques produce reliable deployment and bending of occluder 20 in vivo. An intermediate approach may also be used: tube 25 may be only slightly preformed ex vivo such that it is predisposed to bend into its intended deployed configuration in vivo upon application of forces $F_d$ and $F_p$.

An occluder 20 as described herein may be delivered to an anatomical aperture 18 using any suitable delivery technique. For example, distal side 30 and proximal side 40 of occluder 20 may be deployed in separate steps, or both distal side 30 and proximal side 40 of occluder 20 may be deployed in the same step. One delivery method will be described in detail herein.

Figure 9C:
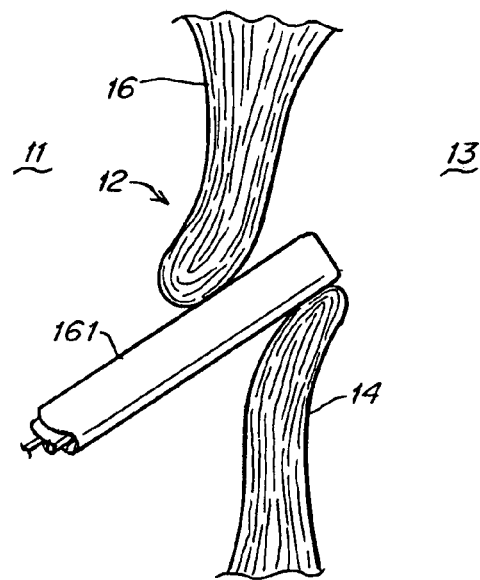
Figure 9D:
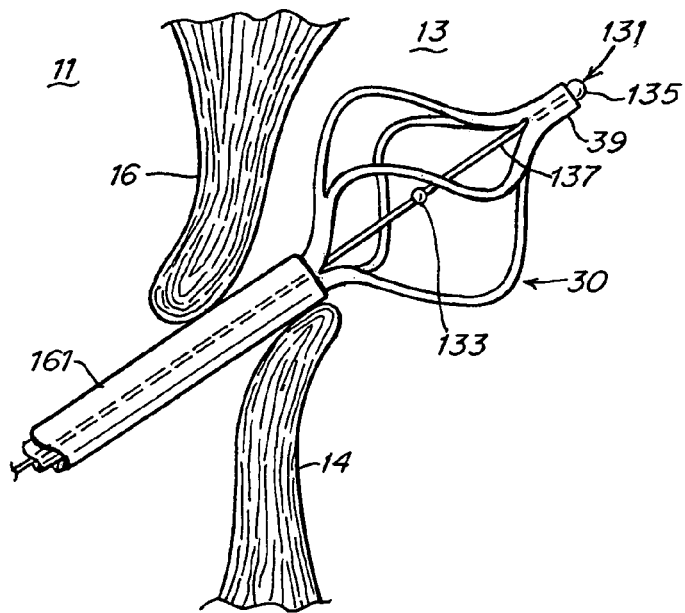
Figure 9E:
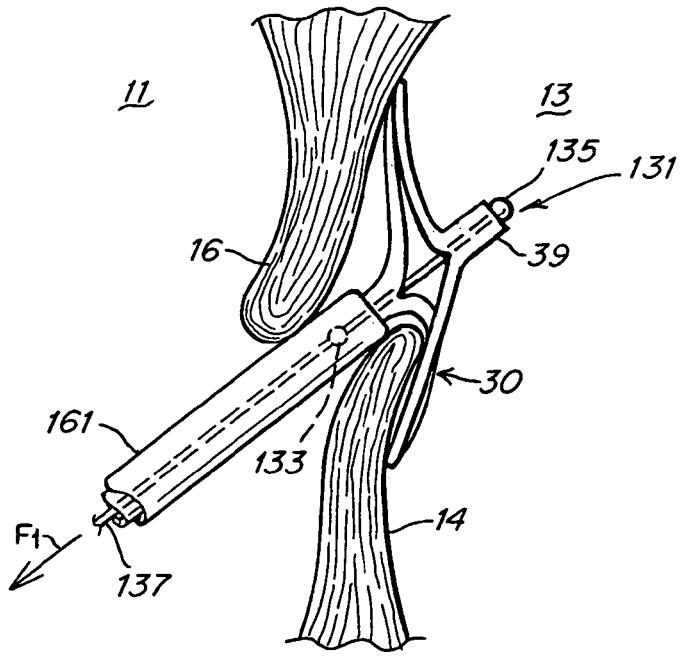
Figure 9F:
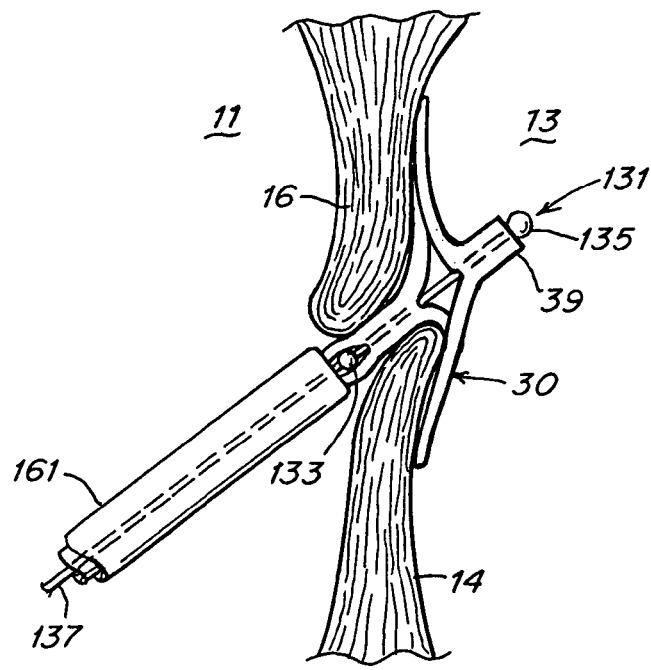
Figure 9G:
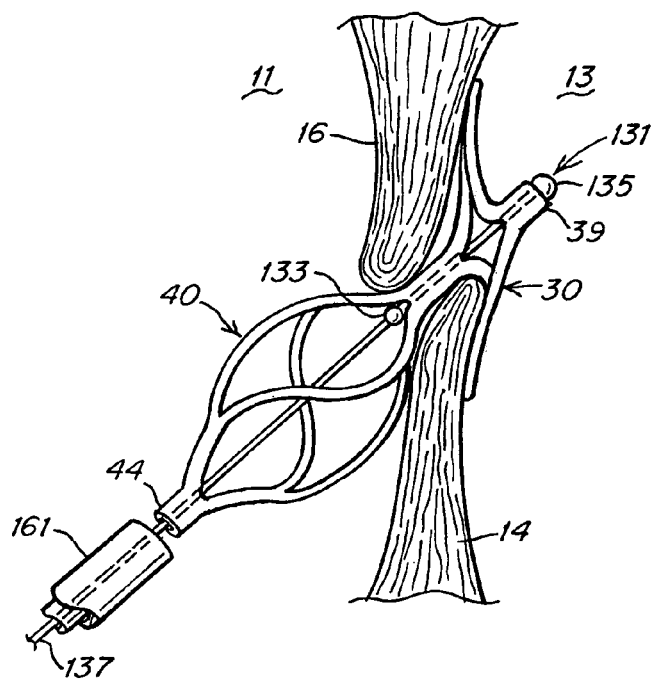
Figure 9H:
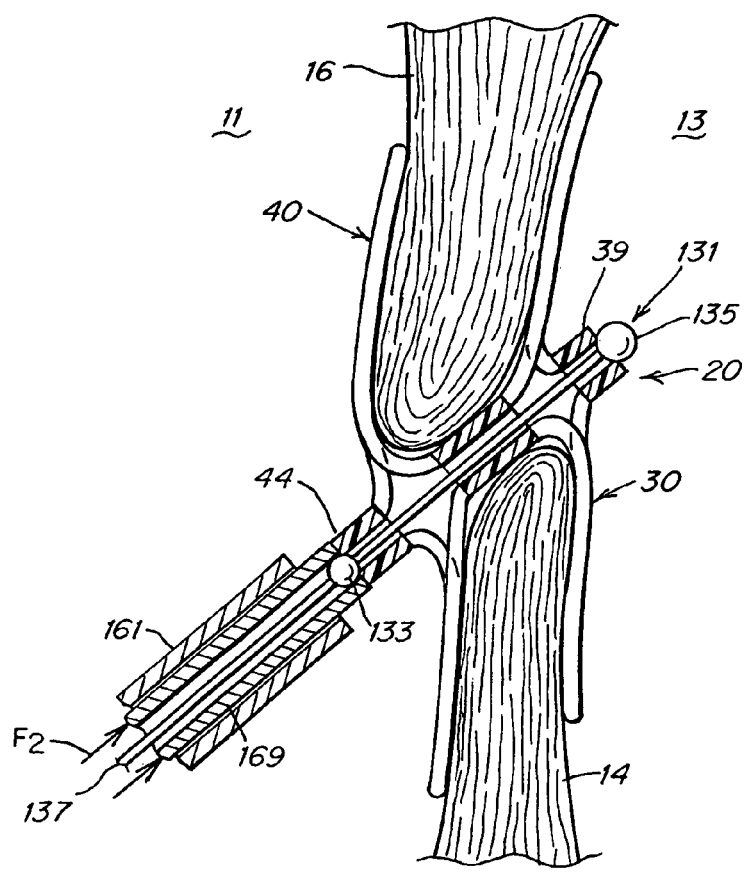

As shown in FIGS. 9A-9H, a delivery sheath 161 containing pusher sleeve 169 (shown in FIG. 9H) is used to deliver occluder 20 including the catch system 131 illustrated in FIGS. 6A-6E. Sheath 161 contains occluder 20 in its elongated, delivery form (FIG. 9A). As shown in FIG. 9B, delivery sheath 161 is first inserted into the right atrium 11 of the patient's heart. Sheath 161 is next inserted through aperture 18 located in the septal tissue 12 (which, in this example, is a PFO tunnel) and into the left atrium 13 (FIG. 9C). Distal side 30 of occluder 20 is then exposed into the left atrium 13, as shown in FIG. 9D. Following deployment of distal side 30, pulling force $F_1$ is applied to delivery string 137 while pusher sleeve 169 is holding the occluder 20 in place such that ball 133 passes through the central tube 22, thereby securing distal side 30 into its deployed state (FIG. 9E). Sheath 161 is further withdrawn through the aperture 18 and into the right atrium 11, such that central tube 22 is deployed through the aperture 18 (FIG. 9F). Proximal side 40 of occluder 20 is then exposed into the right atrium 11 (FIG. 9G), and pulling force $F_1$ is again applied to delivery string 137 while pusher sleeve 169 is holding the occluder 20 in place such that ball 133 passes through tip 44, thereby securing the proximal side 40 into its deployed state (FIG. 9H). When properly deployed, occluder 20 rests within the aperture 18, and the distal side 30 and proximal side 40 exert a compressive force against septum primum 14 and septum secundum 16 in the left 13 and right 11 atria, respectively, to close the aperture 18, i.e. the PFO. When occluder 20 is properly deployed, delivery string 137 is detached from catch system 131, including balls 133 and 135 and a connecting member, and sheath 161 is then withdrawn from the heart. In the event occluder 20 is not properly deployed after performing the procedure described above, the occluder 20 may be recovered by reversing the steps of the above described delivery sequence.

Figure 10A:
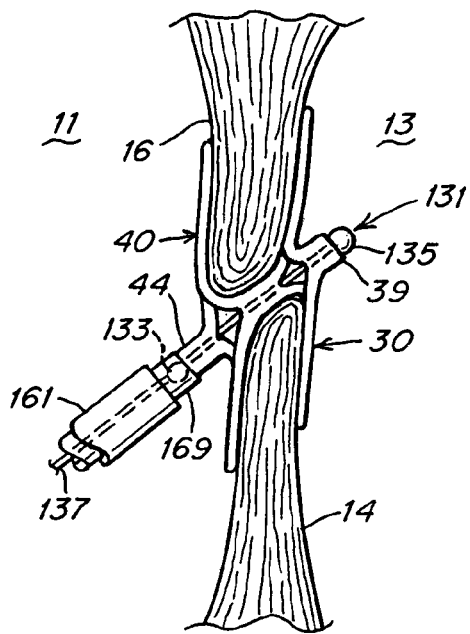
FIGS. 10A-10D are side views of one method for retrieving an occluder according to the present invention from a septal defect.
Figure 10B:
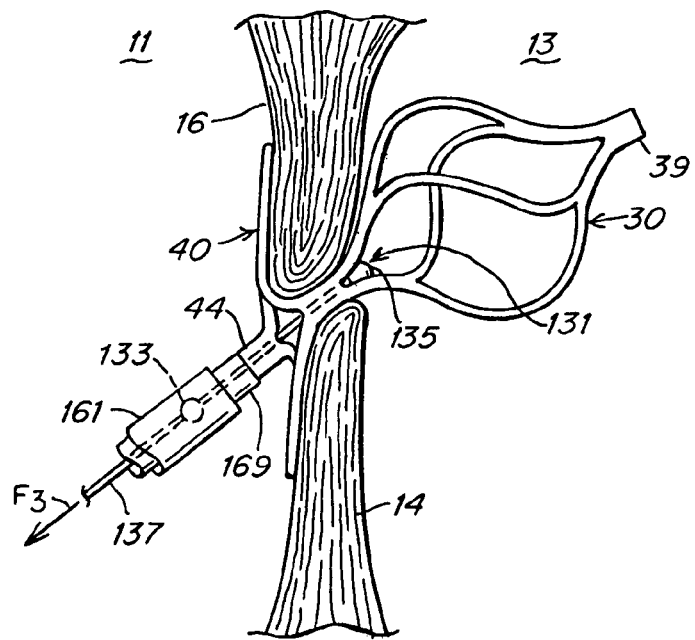
Figure 10C:
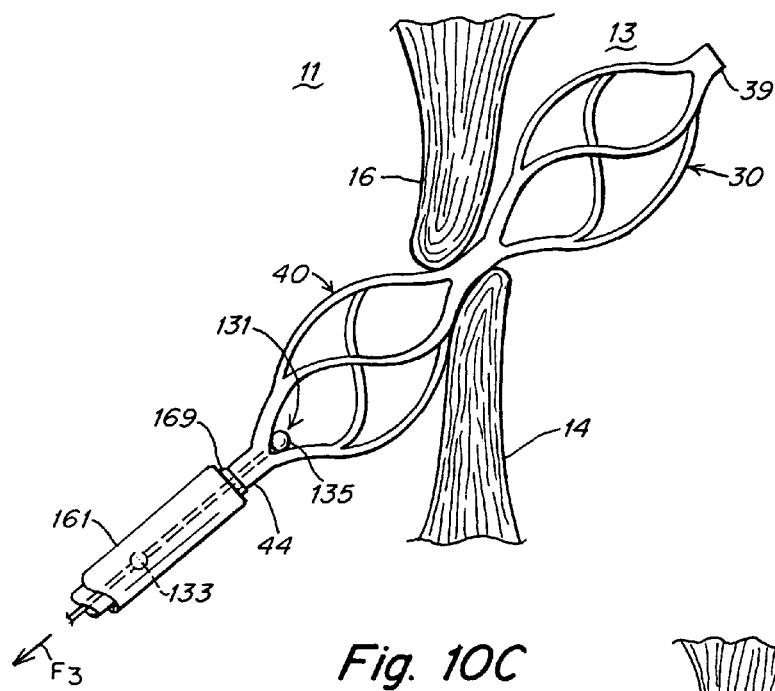
Figure 10D:
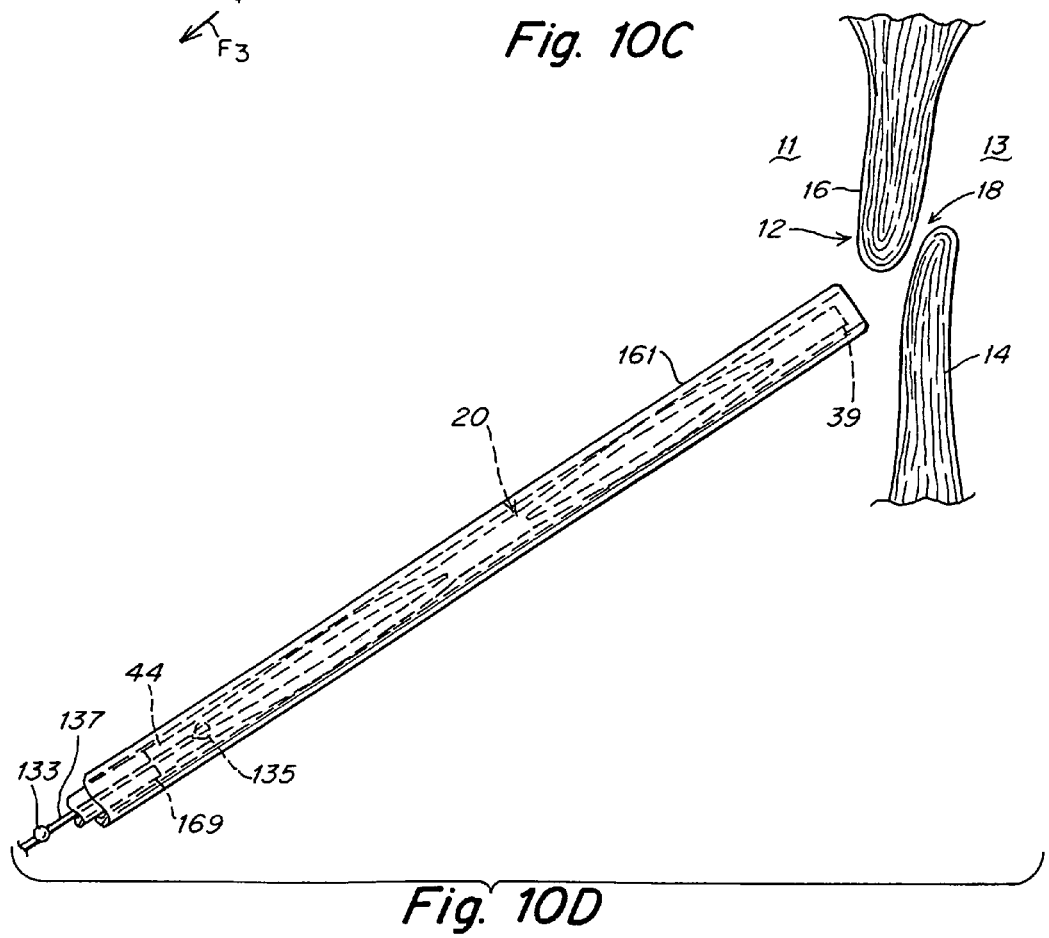

In an alternative recovery technique, the occluder 20 may be recovered and repositioned by catch system 131 as shown in FIGS. 10A-10D. Pusher sleeve 169 in sheath 161 is positioned against tip 44 of the occluder 20 in the right atrium 11 (FIG. 10A). Pulling force $F_2$ is applied to delivery string 137, such that ball 135 passes through end 39 and into central tube 22, thereby releasing distal side 30 from its deployed state (FIG. 10B). Force $F_2$ is again applied to delivery string 137 so that ball 135 subsequently passes through central tube 22, thereby releasing proximal side 40 from its deployed state (FIG. 10C). Delivery string 137 is then pulled further such that occluder 20, now in its elongated state, is retracted into sheath 161 (FIG. 10D). Following recovery of occluder 20, sheath 161 may be withdrawn from the heart and another occluder inserted in the desired delivery location as described above and shown in FIGS. 9A-9H.

One skilled in the art will recognize that the occluders described herein may be used with anti-thrombogenic compounds, including but not limited to heparin and peptides, to reduce thrombogenicity of the occluder and/or to enhance the healing response of the septal tissue 12 following deployment of the occluder in vivo. Similarly, the occluders described herein may be used to deliver other drugs or pharmaceutical agents (e.g. growth factors, peptides). The anti-thrombogenic compounds, drugs, and/or pharmaceutical agents may be included in the occluders of the present invention in several ways, including by incorporation into the tissue scaffold, as previously described, or as a coating, e.g. a polymeric coating, on the tube(s) 25 forming the distal side 30 and proximal side 40 of the occluder 20. Furthermore, the occluders described herein may include cells that have been seeded within the tissue scaffold or coated upon the tube(s) 25 forming the distal side 30 and proximal side 40 of the occluder 20.

One skilled in the art will further recognize that occluders according to this invention could be used to occlude other vascular and non-vascular openings. For example, the device could be inserted into a left atrial appendage or other tunnels or tubular openings within the body.

Having described preferred embodiments of the invention, it should be apparent that various modifications may be made without departing from the spirit and scope of the invention, which is defined in the claims below.

What is claimed is:

1. An occluder for a defect adapted to be introduced into the body through the vasculature, the occluder comprising:
    a tube comprising a proximal side, a central tube portion, and a distal side that cooperate to close the defect, the proximal side having a tip, and the distal side having an end, wherein the proximal and distal sides of the occluder include a plurality of struts, the plurality of struts defining an elongate shape in a first configuration, wherein upon compression of the proximal side and the distal side, the plurality of struts form a plurality of proximal loops and distal loops in a second configuration; and
    a catch system adapted to secure the occluder in a deployed position such that the occluder is not secured during delivery and becomes secured during deployment, the catch system comprising:
        a) a first catch element configured to pass through the central tube portion and the tip upon application of a first pulling force $F_1$ to secure the occluder in the deployed position, wherein the first catch element cannot return through the central portion and tip without application of a sufficient additional force thereto;
        b) a second catch element configured to pass through the end and the central tube portion upon application of a second pulling force $F_2$ to release the distal side and proximal side from the deployed position, wherein the second catch element cannot pass through the tip; and
        c) a wire connecting the first catch element and the second catch element.

2. The occluder of claim 1, wherein the struts extend along a line parallel to the axis of the tube.

3. The occluder of claim 1, wherein at least one of the catch elements is a ball.

4. The occluder of claim 1, wherein the occluder is adapted to be secured in the heart with tissue between the proximal side and the distal side of the occluder.

5. The occluder of claim 1, wherein the loops have identical cross section.

6. The occluder of claim 1, wherein the number of loops formed is 4.

7. The occluder of claim 1, wherein the loops twist when the axial length of the tube is reduced.

8. The occluder of claim 1, wherein the loops align with one another.

9. The occluder of claim 1, wherein the occluder is formed of a bioabsorbable material.

10. The occluder of claim 1, wherein the occluder further comprises tissue scaffolding attached to the loops.

11. The occluder of claim 10, wherein the tissue scaffolding is bioabsorbable.

12. The occluder according to claim 1, where the occluder is formed of nitinol.

* * * * *